US012458525B2

(12) United States Patent
Garvey et al.

(10) Patent No.: US 12,458,525 B2
(45) Date of Patent: Nov. 4, 2025

(54) ACOUSTIC SILENCER FOR A URINE SUCTION SYSTEM

(71) Applicant: PureWick Corporation, El Cajon, CA (US)

(72) Inventors: Tony Garvey, Listowel (IE); Meghan Caracciola, Washington, DC (US); Padraig Fogarty, Ballina-Killaloe (IE); Tamika Richardson, Schenectady, NY (US)

(73) Assignee: PureWick Corporation, Covington, GA (US)

( * ) Notice: Subject to any disclaimer, the term of this patent is extended or adjusted under 35 U.S.C. 154(b) by 221 days.

(21) Appl. No.: 17/653,920

(22) Filed: Mar. 8, 2022

(65) Prior Publication Data

US 2022/0287868 A1 Sep. 15, 2022

Related U.S. Application Data

(60) Provisional application No. 63/159,210, filed on Mar. 10, 2021.

(51) Int. Cl.
*A61F 5/453* (2006.01)
*F04B 39/00* (2006.01)

(52) U.S. Cl.
CPC .......... *A61F 5/453* (2013.01); *F04B 39/0061* (2013.01); *F04B 39/0066* (2013.01); *F04B 39/0072* (2013.01)

(58) Field of Classification Search
CPC .............. F04B 39/0061; F04B 39/0066; F04B 39/0072; A61F 5/453
See application file for complete search history.

(56) References Cited

U.S. PATENT DOCUMENTS 670,602 A 3/1901 Baker
737,443 A * 8/1903 Mooers .................... F01N 1/08 138/42
1,015,905 A 1/1912 Northrop
(Continued)

FOREIGN PATENT DOCUMENTS

AU 2018216821 A1 8/2019
AU 2021299304 A1 2/2023
(Continued)

OTHER PUBLICATIONS

US 9,908,683 B2, 03/2018, Sandhausen et al. (withdrawn)
(Continued)

*Primary Examiner* — Christopher S Bobish
(74) *Attorney, Agent, or Firm* — Ballard Spahr LLP

(57) ABSTRACT

An example urine suction device suitable for extracting urine from a urine collection device is disclosed. The suction device can include a motor, a pump driven by the motor, a conduit, and an acoustic silencer. The pump can extract urine from a urine collection device. The acoustic silencer can be in fluid communication with the pump and conduit. The acoustic silencer can attenuate or reduce one or more acoustic waves generated by the pump and/or the motor. One or more components or structures within the acoustic silencer can at least partially attenuate the acoustic waves as they propagate along a non-linear airflow path defined by the acoustic silencer.

25 Claims, 7 Drawing Sheets

(56) References Cited

U.S. PATENT DOCUMENTS 1,032,841 A 7/1912 Koenig
1,178,644 A 4/1916 Johnson
1,387,726 A 8/1921 Karge
1,742,080 A 12/1929 Jones
1,979,899 A 11/1934 Obrien et al.
2,241,010 A * 5/1941 Chipley ................ F01N 13/007 417/540
2,262,772 A 11/1941 Peder
2,326,881 A 8/1943 Packer
2,379,346 A 6/1945 Farrell
2,485,555 A * 10/1949 Bester ................... F01N 13/082 181/260
2,571,357 A 10/1951 Charles
2,613,670 A 10/1952 Edward
2,616,426 A 11/1952 Adele
2,644,234 A 7/1953 Earl
2,648,335 A 8/1953 Chambers
2,859,786 A 11/1958 Tupper
2,944,551 A 7/1960 Carl
2,968,046 A 1/1961 Duke
2,971,512 A 2/1961 Reinhardt
3,032,038 A 5/1962 Swinn
3,077,883 A 2/1963 Hill
3,087,938 A 4/1963 Hans et al.
3,169,528 A 2/1965 Knox et al.
3,171,506 A * 3/1965 Hald ................... F04B 39/0055 181/403
3,175,719 A 3/1965 Herndon
3,194,238 A 7/1965 Breece
3,198,994 A 8/1965 Hildebrandt et al.
3,221,742 A 12/1965 Egon
3,312,221 A 4/1967 Overment
3,312,981 A 4/1967 McGuire et al.
3,349,768 A 10/1967 Keane
3,362,590 A 1/1968 Gene
3,366,116 A 1/1968 Huck
3,398,848 A 8/1968 Donovan
3,400,717 A 9/1968 Bruce et al.
3,406,688 A 10/1968 Bruce
3,424,163 A 1/1969 Gravdahl
3,425,471 A 2/1969 Yates
3,434,565 A * 3/1969 Fischer ................... F01N 1/023 181/250
3,511,241 A 5/1970 Lee
3,512,185 A 5/1970 Ellis
3,520,300 A 7/1970 Flower
3,528,423 A 9/1970 Lee
3,613,123 A 10/1971 Langstrom
3,648,700 A 3/1972 Warner
3,651,810 A 3/1972 Ormerod
3,661,155 A 5/1972 Lindan
3,683,918 A 8/1972 Pizzella
3,699,815 A 10/1972 Holbrook
3,726,277 A 4/1973 Hirschman
3,742,952 A 7/1973 Magers et al.
3,757,355 A 9/1973 Allen et al.
3,788,324 A 1/1974 Lim
3,843,016 A 10/1974 Bornhorst et al.
3,863,638 A 2/1975 Rogers et al.
3,863,798 A 2/1975 Kurihara et al.
3,864,759 A 2/1975 Horiuchi
3,865,109 A 2/1975 Elmore et al.
3,881,486 A 5/1975 Fenton
3,881,489 A 5/1975 Hartwell
3,915,189 A 10/1975 Holbrook et al.
3,998,228 A 12/1976 Poidomani
3,999,550 A 12/1976 Martin
4,006,793 A * 2/1977 Robinson .................. F01N 1/00 181/266
4,015,604 A 4/1977 Csillag
4,020,843 A 5/1977 Kanall
4,022,213 A 5/1977 Stein
4,027,776 A 6/1977 Douglas
4,064,962 A * 12/1977 Hunt ......................... F01N 1/02 181/272
4,096,897 A 6/1978 Cammarata
4,116,197 A 9/1978 Bermingham
4,180,178 A 12/1979 Turner
4,187,953 A 2/1980 Turner
4,194,508 A 3/1980 Anderson
4,200,102 A 4/1980 Duhamel et al.
4,202,058 A 5/1980 Anderson
4,203,503 A * 5/1980 Franco .................... F01N 1/089 181/275
4,209,076 A * 6/1980 Franco ...................... F01N 1/02 181/275
4,223,677 A 9/1980 Anderson
4,233,025 A 11/1980 Larson et al.
4,233,978 A 11/1980 Hickey
4,246,901 A 1/1981 Frosch et al.
4,253,542 A * 3/1981 Ruspa ....................... E02F 9/00 181/275
4,257,418 A 3/1981 Hessner
4,270,539 A 6/1981 Frosch et al.
4,281,655 A 8/1981 Terauchi
4,292,916 A 10/1981 Bradley et al.
4,330,239 A * 5/1982 Gannaway ............. F01N 1/089 181/403
4,352,356 A 10/1982 Tong
4,360,933 A 11/1982 Kimura et al.
4,365,363 A 12/1982 Windauer
4,375,841 A * 3/1983 Vielbig ................... F01N 1/083 181/272
4,387,726 A 6/1983 Denard
4,403,991 A 9/1983 Hill
4,425,130 A 1/1984 Desmarais
4,446,986 A 5/1984 Bowen et al.
4,453,938 A 6/1984 Brendling
4,457,314 A 7/1984 Knowles
4,476,879 A 10/1984 Jackson
4,526,688 A 7/1985 Schmidt et al.
4,528,703 A 7/1985 Kraus
D280,438 S 9/1985 Wendt
4,551,141 A 11/1985 Mcneil
4,553,968 A 11/1985 Komis
4,581,026 A 4/1986 Schneider
4,589,516 A * 5/1986 Inoue .................. F01N 13/1861 181/282
4,601,716 A 7/1986 Smith
4,610,675 A 9/1986 Triunfol
4,620,333 A 11/1986 Ritter
4,626,250 A 12/1986 Schneider
4,627,846 A 12/1986 Ternstroem
4,631,061 A * 12/1986 Martin .................... A61F 5/451 604/323
4,650,477 A 3/1987 Johnson
4,655,754 A 4/1987 Richmond et al.
4,656,675 A 4/1987 Fajnsztajn
4,681,570 A 7/1987 Dalton
4,681,577 A 7/1987 Stern et al.
4,692,160 A 9/1987 Nussbaumer
4,707,864 A 11/1987 Ikematsu et al.
4,713,065 A 12/1987 Koot
4,713,066 A 12/1987 Komis
4,723,953 A 2/1988 Pratt et al.
4,735,841 A 4/1988 Sourdet
4,743,236 A 5/1988 Manschot
4,747,166 A 5/1988 Kuntz
4,752,944 A 6/1988 Conrads et al.
4,769,215 A 9/1988 Ehrenkranz
4,771,484 A 9/1988 Mozell
4,772,280 A 9/1988 Rooyakkers
4,784,654 A 11/1988 Beecher
4,790,830 A 12/1988 Hamacher
4,790,835 A 12/1988 Elias
4,791,686 A 12/1988 Taniguchi et al.
4,795,449 A 1/1989 Schneider et al.
4,798,603 A 1/1989 Meyer et al.
4,799,928 A 1/1989 Crowley
4,804,377 A 2/1989 Hanifl et al.
4,812,053 A 3/1989 Bhattacharjee

(56) References Cited

U.S. PATENT DOCUMENTS 4,813,943 A 3/1989 Smith
4,820,291 A 4/1989 Terauchi et al.
4,820,297 A 4/1989 Kaufman et al.
4,841,728 A * 6/1989 Jean ........................ F01N 1/089 181/266
4,846,818 A 7/1989 Keldahl et al.
4,846,819 A 7/1989 Welch
4,846,909 A 7/1989 Klug et al.
4,865,595 A 9/1989 Heyden
4,880,417 A 11/1989 Yabrov et al.
4,882,794 A 11/1989 Stewart
4,883,465 A 11/1989 Brennan
4,886,498 A 12/1989 Newton
4,886,508 A 12/1989 Washington
4,886,509 A 12/1989 Mattsson
4,889,532 A 12/1989 Metz et al.
4,889,533 A 12/1989 Beecher
4,890,691 A * 1/1990 Ching-Ho ............... F01N 1/085 181/272
4,903,254 A 2/1990 Haas
4,904,248 A 2/1990 Vaillancourt
4,905,692 A 3/1990 More
4,911,262 A * 3/1990 Tani ........................ F01N 1/089 181/266
4,936,838 A 6/1990 Cross et al.
4,950,262 A 8/1990 Takagi
4,955,922 A 9/1990 Terauchi
4,957,487 A 9/1990 Gerow
4,965,460 A 10/1990 Tanaka et al.
4,986,823 A 1/1991 Anderson et al.
4,987,849 A 1/1991 Sherman
5,002,541 A 3/1991 Conkling et al.
5,004,463 A 4/1991 Nigay
5,013,308 A 5/1991 Sullivan et al.
5,031,248 A 7/1991 Kemper
5,045,077 A 9/1991 Blake
5,045,283 A 9/1991 Patel
5,049,144 A 9/1991 Payton
5,053,339 A 10/1991 Patel
5,057,092 A 10/1991 Webster
5,058,088 A 10/1991 Haas et al.
5,071,347 A 12/1991 McGuire
5,078,707 A 1/1992 Peter
5,084,037 A 1/1992 Barnett
5,100,396 A 3/1992 Zamierowski
5,112,324 A 5/1992 Wallace
5,147,301 A 9/1992 Ruvio
5,176,667 A 1/1993 Debring
5,195,997 A 3/1993 Carns
5,196,654 A * 3/1993 DiFlora ................... F01N 1/089 181/255
5,203,699 A 4/1993 McGuire
5,244,458 A 9/1993 Takasu
5,246,454 A 9/1993 Peterson
5,267,988 A 12/1993 Farkas
5,275,307 A 1/1994 Freese
5,282,795 A 2/1994 Finney
5,294,983 A 3/1994 Ersoz et al.
5,295,979 A 3/1994 Delaurentis et al.
5,295,983 A 3/1994 Kubo
5,300,052 A 4/1994 Kubo
5,304,749 A * 4/1994 Crandell ................. F01N 1/083 181/269
5,312,383 A 5/1994 Kubalak
5,318,550 A 6/1994 Cermak et al.
5,330,459 A 7/1994 Lavon et al.
5,340,840 A 8/1994 Park et al.
5,382,244 A 1/1995 Telang
5,409,014 A 4/1995 Napoli et al.
5,409,475 A 4/1995 Steer
5,411,495 A 5/1995 Willingham
5,423,784 A 6/1995 Metz
5,456,246 A 10/1995 Schmieding et al.
5,466,229 A 11/1995 Elson et al.
5,478,334 A 12/1995 Bernstein
5,499,977 A 3/1996 Marx
5,543,042 A 8/1996 Filan et al.
D373,928 S 9/1996 Green
5,582,604 A 12/1996 Ahr et al.
5,592,950 A 1/1997 Kopelowicz
5,593,389 A 1/1997 Chang
5,605,161 A 2/1997 Cross
5,614,699 A * 3/1997 Yashiro ................... F01N 1/089 181/254
5,618,277 A 4/1997 Goulter
5,628,735 A 5/1997 Skow
5,636,643 A 6/1997 Argenta et al.
5,637,104 A 6/1997 Ball et al.
5,674,212 A 10/1997 Osborn et al.
5,678,564 A 10/1997 Lawrence et al.
5,678,654 A 10/1997 Uzawa
5,687,429 A 11/1997 Rahlff
5,695,485 A 12/1997 Duperret et al.
5,700,254 A 12/1997 Mcdowall et al.
5,701,612 A 12/1997 Daneshvar
5,705,777 A * 1/1998 Flanigan ................. F01N 13/18 181/282
5,735,835 A 4/1998 Holland
5,752,944 A 5/1998 Dann et al.
5,763,333 A 6/1998 Suzuki et al.
5,772,644 A 6/1998 Bark et al.
5,792,132 A 8/1998 Garcia
5,827,243 A 10/1998 Palestrant
5,827,247 A 10/1998 Kay
5,827,250 A 10/1998 Fujioka et al.
5,827,257 A 10/1998 Fujioka et al.
D401,699 S 11/1998 Herchenbach et al.
5,859,393 A * 1/1999 Cummins, Jr. ........... F01N 1/04 181/275
5,865,378 A 2/1999 Hollinshead et al.
5,876,393 A 3/1999 Ahr et al.
5,887,291 A 3/1999 Bellizzi
5,891,125 A 4/1999 Plumley
5,894,608 A 4/1999 Birbara
D409,303 S 5/1999 Oepping
5,911,222 A 6/1999 Lawrence et al.
5,957,904 A 9/1999 Holland
5,968,026 A 10/1999 Osborn et al.
5,972,505 A 10/1999 Phillips et al.
6,007,526 A 12/1999 Passalaqua et al.
6,039,060 A 3/2000 Rower
6,050,983 A 4/2000 Moore et al.
6,059,762 A 5/2000 Boyer et al.
6,063,064 A 5/2000 Tuckey et al.
6,098,625 A 8/2000 Winkler
6,105,174 A 8/2000 Karlsten et al.
6,113,582 A 9/2000 Dwork
6,117,163 A 9/2000 Bierman
6,123,398 A 9/2000 Arai et al.
6,129,718 A 10/2000 Wada et al.
6,131,964 A 10/2000 Sareshwala
6,152,902 A 11/2000 Christian et al.
6,164,569 A 12/2000 Hollinshead et al.
6,177,606 B1 1/2001 Etheredge et al.
6,209,142 B1 4/2001 Mattsson et al.
6,220,050 B1 * 4/2001 Cooksey ................. F04B 39/04 62/503
6,244,311 B1 * 6/2001 Hand ...................... A61M 1/63 141/366
6,248,096 B1 6/2001 Dwork et al.
6,263,887 B1 7/2001 Dunn
6,283,246 B1 * 9/2001 Nishikawa ................ F01N 1/08 181/255
6,296,627 B1 10/2001 Edwards
6,311,339 B1 11/2001 Kraus
6,336,919 B1 1/2002 Davis et al.
6,338,729 B1 1/2002 Wada et al.
6,352,525 B1 3/2002 Wakabayashi
6,394,988 B1 5/2002 Hashimoto
6,398,742 B1 6/2002 Kim
6,406,463 B1 6/2002 Brown
6,409,712 B1 6/2002 Dutari et al.

(56) References Cited

U.S. PATENT DOCUMENTS 6,415,888 B2 * 7/2002 An .......................... F01N 1/12 181/281
6,416,500 B1 7/2002 Wada et al.
6,423,045 B1 7/2002 Wise et al.
6,428,521 B1 8/2002 Droll
6,428,522 B1 8/2002 Dipalma et al.
6,446,454 B1 * 9/2002 Lee .................... F04B 39/0061 181/403
6,467,570 B1 * 10/2002 Herold ..................... F01N 1/02 181/269
6,475,198 B1 11/2002 Lipman et al.
6,479,726 B1 11/2002 Cole et al.
6,491,673 B1 12/2002 Palumbo et al.
6,508,794 B1 1/2003 Palumbo et al.
6,524,292 B1 2/2003 Dipalma et al.
6,540,729 B1 4/2003 Wada et al.
6,547,771 B2 4/2003 Robertson et al.
6,551,293 B1 4/2003 Mitchell
6,569,133 B2 5/2003 Cheng et al.
D476,518 S 7/2003 Doppelt
6,592,560 B2 7/2003 Snyder et al.
6,610,038 B1 8/2003 Dipalma et al.
6,618,868 B2 9/2003 Minnick
6,620,142 B1 9/2003 Flueckiger
6,629,651 B1 10/2003 Male et al.
6,635,037 B1 10/2003 Bennett
6,635,038 B2 10/2003 Scovel
6,652,495 B1 11/2003 Walker
6,666,850 B1 12/2003 Ahr et al.
6,685,684 B1 2/2004 Falconer
6,695,828 B1 2/2004 Dipalma et al.
6,699,174 B1 3/2004 Bennett
6,700,034 B1 3/2004 Lindsay et al.
6,702,793 B1 3/2004 Sweetser et al.
6,706,027 B2 3/2004 Harvie et al.
6,732,384 B2 5/2004 Scott
6,736,977 B1 5/2004 Hall et al.
6,740,066 B2 5/2004 Wolff et al.
6,764,477 B1 7/2004 Chen et al.
6,783,519 B2 8/2004 Samuelsson
6,796,974 B2 9/2004 Palumbo et al.
6,814,547 B2 11/2004 Childers et al.
6,849,065 B2 2/2005 Schmidt et al.
6,857,137 B2 2/2005 Otto
6,885,690 B2 4/2005 Aggerstam et al.
6,888,044 B2 5/2005 Fell et al.
6,893,425 B2 5/2005 Dunn et al.
6,912,737 B2 7/2005 Ernest et al.
6,918,899 B2 7/2005 Harvie
6,979,324 B2 12/2005 Bybordi et al.
7,018,366 B2 3/2006 Easter
7,066,411 B2 6/2006 Male et al.
7,122,023 B1 10/2006 Hinoki
7,125,399 B2 10/2006 Miskie
7,131,964 B2 11/2006 Harvie
7,135,012 B2 11/2006 Harvie
7,141,043 B2 11/2006 Harvie
D533,972 S 12/2006 La
7,160,273 B2 1/2007 Greter et al.
7,166,092 B2 1/2007 Elson et al.
7,171,699 B2 2/2007 Ernest et al.
7,171,871 B2 2/2007 Kozak
7,179,951 B2 2/2007 Krishnaswamy-Mirle et al.
7,181,781 B1 2/2007 Trabold et al.
7,186,245 B1 3/2007 Cheng et al.
7,192,424 B2 3/2007 Cooper
7,219,764 B1 * 5/2007 Forbes ................... F01N 1/085 181/272
7,220,250 B2 5/2007 Suzuki et al.
D562,975 S 2/2008 Otto
7,335,189 B2 2/2008 Harvie
7,358,282 B2 4/2008 Krueger et al.
7,390,320 B2 6/2008 Machida et al.
7,438,706 B2 10/2008 Koizumi et al.
7,488,310 B2 2/2009 Yang
7,491,194 B1 2/2009 Oliwa
D591,106 S 4/2009 Dominique et al.
7,513,381 B2 4/2009 Heng et al.
7,520,872 B2 4/2009 Biggie et al.
D593,801 S 6/2009 Wilson et al.
7,540,364 B2 6/2009 Sanderson
7,549,511 B2 * 6/2009 Marocco .................. F01N 1/08 181/275
7,549,512 B2 * 6/2009 Newberry ................ F01N 1/08 181/281
7,585,293 B2 9/2009 Vermaak
7,588,560 B1 9/2009 Dunlop
7,637,905 B2 12/2009 Saadat et al.
7,658,730 B2 2/2010 Conley
7,665,359 B2 2/2010 Barber
7,682,347 B2 3/2010 Parks et al.
7,687,004 B2 3/2010 Allen
7,695,459 B2 4/2010 Gilbert et al.
7,695,460 B2 4/2010 Wada et al.
7,699,818 B2 4/2010 Gilbert
7,699,831 B2 4/2010 Bengtson et al.
7,722,584 B2 * 5/2010 Tanaka ................. A61M 1/782 604/326
7,727,206 B2 6/2010 Gorres
7,740,620 B2 6/2010 Gilbert et al.
7,749,205 B2 7/2010 Tazoe et al.
7,755,497 B2 7/2010 Wada et al.
7,766,887 B2 8/2010 Burns et al.
D625,407 S 10/2010 Koizumi et al.
7,806,879 B2 10/2010 Brooks et al.
7,811,272 B2 10/2010 Lindsay et al.
7,815,067 B2 10/2010 Matsumoto et al.
7,833,169 B2 11/2010 Hannon
7,857,806 B2 * 12/2010 Karpowicz ............ A61M 1/74 604/304
7,866,942 B2 1/2011 Harvie
7,871,385 B2 1/2011 Levinson et al.
7,875,010 B2 1/2011 Frazier et al.
7,901,389 B2 3/2011 Mombrinie
7,927,320 B2 4/2011 Goldwasser et al.
7,927,321 B2 4/2011 Marland
7,931,634 B2 4/2011 Swiecicki et al.
7,939,706 B2 5/2011 Okabe et al.
7,946,443 B2 5/2011 Stull et al.
7,947,025 B2 5/2011 Buglino et al.
7,963,419 B2 6/2011 Burney et al.
7,976,519 B2 7/2011 Bubb et al.
7,993,318 B2 8/2011 Olsson et al.
8,015,627 B2 9/2011 Baker et al.
8,016,071 B1 * 9/2011 Martinus ............ F04B 39/0061 181/275
8,028,460 B2 10/2011 Williams
8,047,398 B2 11/2011 Dimartino et al.
8,083,094 B2 12/2011 Caulfield et al.
8,128,608 B2 3/2012 Thevenin
8,181,651 B2 5/2012 Pinel
8,181,819 B2 5/2012 Burney et al.
8,211,063 B2 7/2012 Bierman et al.
8,221,369 B2 7/2012 Parks et al.
8,241,262 B2 8/2012 Mahnensmith
8,277,426 B2 10/2012 Wilcox et al.
8,287,508 B1 10/2012 Sanchez
8,303,554 B2 11/2012 Tsai et al.
8,322,565 B2 12/2012 Caulfield et al.
8,337,477 B2 12/2012 Parks et al.
D674,241 S 1/2013 Bickert et al.
8,343,122 B2 1/2013 Gorres
8,343,125 B2 1/2013 Kawazoe et al.
8,353,074 B2 1/2013 Krebs
8,353,886 B2 1/2013 Bester et al.
D676,241 S 2/2013 Merrill
8,388,587 B1 3/2013 Gmuer et al.
8,388,588 B2 3/2013 Wada et al.
D679,807 S 4/2013 Burgess et al.
8,425,482 B2 4/2013 Khoubnazar
8,434,586 B2 * 5/2013 Pawelski .............. F04C 29/065 181/175
8,449,510 B2 5/2013 Martini et al.
D684,260 S 6/2013 Lund et al.

(56) References Cited

U.S. PATENT DOCUMENTS 8,470,230 B2 6/2013 Caulfield et al.
8,479,941 B2 7/2013 Matsumoto et al.
8,479,949 B2 7/2013 Henkel
8,500,719 B1 8/2013 Simpson et al.
8,512,301 B2 8/2013 Ma
8,529,530 B2 9/2013 Koch et al.
8,535,284 B2 9/2013 Joder et al.
8,546,639 B2 10/2013 Wada et al.
8,551,075 B2 10/2013 Bengtson
8,568,376 B2 10/2013 Delattre et al.
D694,404 S 11/2013 Burgess et al.
8,585,683 B2 11/2013 Bengtson et al.
8,652,112 B2 2/2014 Johannison et al.
8,669,412 B2 3/2014 Fernkvist et al.
D702,973 S 4/2014 Norland et al.
8,703,032 B2 4/2014 Menon et al.
D704,330 S 5/2014 Cicatelli
D704,510 S 5/2014 Mason et al.
D705,423 S 5/2014 Walsh Cutler
D705,926 S 5/2014 Burgess et al.
8,714,394 B2 5/2014 Wulf
8,715,267 B2 5/2014 Bengtson et al.
8,757,425 B2 6/2014 Copeland
8,777,032 B2 7/2014 Biesecker et al.
8,808,260 B2 8/2014 Koch et al.
8,864,730 B2 10/2014 Conway et al.
8,881,923 B2 11/2014 Higginson
8,882,731 B2 11/2014 Suzuki et al.
8,936,585 B2 1/2015 Carson et al.
D729,581 S 5/2015 Boroski
9,028,460 B2 5/2015 Medeiros
9,056,698 B2 6/2015 Noer
9,078,792 B2 7/2015 Ruiz
9,145,879 B2 * 9/2015 Pirovano ............. F04B 39/0061
9,173,602 B2 11/2015 Gilbert
9,173,799 B2 11/2015 Tanimoto et al.
9,187,220 B2 11/2015 Biesecker et al.
9,199,772 B2 12/2015 Krippendorf
9,233,020 B2 1/2016 Matsumiya
9,248,058 B2 2/2016 Conway et al.
9,308,118 B1 4/2016 Dupree et al.
9,309,029 B2 4/2016 Incorvia et al.
9,333,281 B2 5/2016 Giezendanner et al.
9,381,108 B2 * 7/2016 Longoni ................ A61B 5/201
9,382,047 B2 7/2016 Schmidtner et al.
9,402,424 B2 8/2016 Roy
9,456,937 B2 10/2016 Ellis
9,480,595 B2 11/2016 Baham et al.
9,517,865 B2 12/2016 Albers et al.
D777,941 S 1/2017 Piramoon
9,533,806 B2 1/2017 Ding et al.
9,550,611 B2 1/2017 Hodge
9,555,930 B2 1/2017 Campbell et al.
9,623,159 B2 4/2017 Locke
D789,522 S 6/2017 Burgess et al.
9,687,849 B2 6/2017 Bruno et al.
9,694,949 B2 7/2017 Hendricks et al.
9,709,048 B2 * 7/2017 Kinjo ...................... F04B 35/04
9,713,547 B2 7/2017 Lee et al.
9,732,754 B2 * 8/2017 Huang ................ F04B 39/0061
9,752,564 B2 * 9/2017 Arceno ............... F04B 39/0055
9,788,992 B2 10/2017 Harvie
D804,907 S 12/2017 Sandoval
9,868,564 B2 1/2018 McGirr et al.
D814,239 S 4/2018 Arora
D817,484 S 5/2018 Lafond
10,037,640 B2 7/2018 Gordon
10,058,470 B2 8/2018 Phillips
10,098,990 B2 10/2018 Koch et al.
D835,264 S 12/2018 Mozzicato et al.
D835,779 S 12/2018 Mozzicato et al.
D840,533 S 2/2019 Mozzicato et al.
D840,534 S 2/2019 Mozzicato et al.
10,225,376 B2 3/2019 Perez Martinez
10,226,376 B2 3/2019 Sanchez et al.
10,258,517 B1 4/2019 Maschino et al.
D848,612 S 5/2019 Mozzicato et al.
10,307,305 B1 6/2019 Hodges
10,335,121 B2 7/2019 Desai
D856,512 S 8/2019 Cowart et al.
10,376,406 B2 8/2019 Newton
10,376,407 B2 8/2019 Newton
10,390,989 B2 8/2019 Sanchez et al.
D858,144 S 9/2019 Fu
10,406,039 B2 9/2019 Villarreal
10,407,222 B2 9/2019 Allen
10,478,356 B2 11/2019 Griffin
10,500,108 B1 12/2019 Maschino et al.
10,502,198 B2 * 12/2019 Stumpf ............... F04B 39/0061
10,538,366 B2 1/2020 Pentelovitch et al.
10,569,938 B2 2/2020 Zhao et al.
10,577,156 B2 3/2020 Dagnelie et al.
RE47,930 E * 4/2020 Cho .................... F04B 39/0072
10,618,721 B2 4/2020 Vazin
D884,390 S 5/2020 Wang
10,669,079 B2 6/2020 Freedman et al.
D892,315 S 8/2020 Airy
10,730,672 B2 8/2020 Bertram et al.
10,737,848 B2 8/2020 Philip et al.
10,765,854 B2 9/2020 Law et al.
10,766,670 B2 9/2020 Kittmann
10,799,386 B1 10/2020 Harrison
10,806,642 B2 10/2020 Tagomori et al.
D901,214 S 11/2020 Hu
10,849,799 B2 12/2020 Nishikawa et al.
10,857,025 B2 12/2020 Davis et al.
10,865,017 B1 12/2020 Cowart et al.
10,889,412 B2 1/2021 West et al.
10,913,581 B2 2/2021 Stahlecker
D912,244 S 3/2021 Rehm et al.
10,952,889 B2 3/2021 Newton et al.
10,973,378 B2 4/2021 Ryu et al.
10,973,678 B2 4/2021 Newton et al.
10,974,874 B2 4/2021 Ragias et al.
11,000,401 B2 5/2021 Ecklund et al.
11,002,165 B2 * 5/2021 Poulin ..................... F01N 1/083
D923,365 S 6/2021 Wang
11,026,829 B2 6/2021 Harvie
11,027,900 B2 6/2021 Liu
11,045,346 B2 6/2021 Argent et al.
D928,946 S 8/2021 Sanchez et al.
11,090,183 B2 8/2021 Sanchez et al.
11,160,695 B2 11/2021 Febo et al.
11,160,697 B2 11/2021 Maschino et al.
11,168,420 B2 11/2021 Kinugasa et al.
11,179,506 B2 11/2021 Barr et al.
11,199,116 B2 * 12/2021 Ostromecki ............ F01N 1/085
11,207,206 B2 12/2021 Sharma et al.
11,226,376 B2 1/2022 Yamauchi et al.
11,253,389 B2 2/2022 Sharma et al.
11,253,407 B2 2/2022 Miao et al.
11,326,586 B2 * 5/2022 Milner ................ F04B 39/0055
11,369,508 B2 6/2022 Ecklund et al.
11,369,524 B2 6/2022 Hubbard et al.
11,376,152 B2 7/2022 Sanchez et al.
11,382,786 B2 7/2022 Sanchez et al.
11,382,788 B2 7/2022 Hjorth et al.
11,389,318 B2 7/2022 Radl et al.
11,395,871 B2 7/2022 Radl et al.
11,399,990 B2 8/2022 Suyama
11,426,303 B2 8/2022 Davis et al.
11,504,265 B2 11/2022 Godinez et al.
11,529,252 B2 12/2022 Glithero et al.
11,547,788 B2 1/2023 Radl et al.
11,806,266 B2 11/2023 Sanchez et al.
11,839,567 B2 12/2023 Davis et al.
D1,010,109 S 1/2024 Ecklund et al.
11,857,716 B2 * 1/2024 Lee ......................... A61M 1/73
11,865,030 B2 1/2024 Davis et al.
11,890,221 B2 2/2024 Ulreich et al.
11,925,575 B2 3/2024 Newton
11,938,053 B2 3/2024 Austermann et al.
11,944,740 B2 4/2024 Hughett et al.
11,994,122 B2 * 5/2024 Bodain ............... F04B 39/0027

(56) References Cited

U.S. PATENT DOCUMENTS

| | | | |
|---|---|---|---|
| 11,998,475 | B2 | 6/2024 | Becker et al. |
| 12,023,457 | B2 | 7/2024 | Mann et al. |
| 12,042,422 | B2 | 7/2024 | Davis et al. |
| D1,038,385 | S | 8/2024 | Ecklund et al. |
| 12,090,083 | B2 | 9/2024 | Ecklund et al. |
| 12,133,813 | B2 | 11/2024 | Ulreich et al. |
| 12,138,195 | B2 | 11/2024 | Alder et al. |
| 2001/0037097 | A1 | 11/2001 | Cheng et al. |
| 2001/0054426 | A1 | 12/2001 | Knudson et al. |
| 2002/0019614 | A1 | 2/2002 | Woon |
| 2002/0026161 | A1 | 2/2002 | Grundke |
| 2002/0026163 | A1 | 2/2002 | Grundke |
| 2002/0087131 | A1 | 7/2002 | Wolff et al. |
| 2002/0091364 | A1 | 7/2002 | Prabhakar |
| 2002/0189992 | A1 | 12/2002 | Schmidt et al. |
| 2002/0193760 | A1 | 12/2002 | Thompson |
| 2002/0193762 | A1 | 12/2002 | Suydam |
| 2003/0004436 | A1 | 1/2003 | Schmidt et al. |
| 2003/0032931 | A1 | 2/2003 | Grundke et al. |
| 2003/0032944 | A1 | 2/2003 | Cawood |
| 2003/0073964 | A1 | 4/2003 | Palumbo et al. |
| 2003/0120178 | A1 | 6/2003 | Heki |
| 2003/0157859 | A1 | 8/2003 | Ishikawa |
| 2003/0181880 | A1 | 9/2003 | Schwartz |
| 2003/0195484 | A1 | 10/2003 | Harvie |
| 2003/0204173 | A1 | 10/2003 | Burns et al. |
| 2003/0233079 | A1 | 12/2003 | Parks et al. |
| 2004/0006321 | A1 | 1/2004 | Cheng et al. |
| 2004/0015141 | A1 | 1/2004 | Cheng et al. |
| 2004/0056122 | A1 | 3/2004 | Male et al. |
| 2004/0084465 | A1 | 5/2004 | Luburic |
| 2004/0127872 | A1 | 7/2004 | Petryk et al. |
| 2004/0128749 | A1 | 7/2004 | Scott |
| 2004/0143229 | A1 | 7/2004 | Easter |
| 2004/0147863 | A1 | 7/2004 | Diaz et al. |
| 2004/0147894 | A1 | 7/2004 | Mizutani et al. |
| 2004/0158221 | A1 | 8/2004 | Mizutani et al. |
| 2004/0176731 | A1 | 9/2004 | Cheng et al. |
| 2004/0176746 | A1 | 9/2004 | Forral |
| 2004/0191919 | A1 | 9/2004 | Unger et al. |
| 2004/0200936 | A1 | 10/2004 | Opperthauser |
| 2004/0207530 | A1 | 10/2004 | Nielsen |
| 2004/0236292 | A1 | 11/2004 | Tazoe et al. |
| 2004/0243075 | A1 | 12/2004 | Harvie |
| 2004/0254547 | A1 | 12/2004 | Okabe et al. |
| 2005/0010182 | A1 | 1/2005 | Parks et al. |
| 2005/0010197 | A1 | 1/2005 | Lau et al. |
| 2005/0033248 | A1 | 2/2005 | Machida et al. |
| 2005/0065471 | A1 | 3/2005 | Kuntz |
| 2005/0070861 | A1 | 3/2005 | Okabe et al. |
| 2005/0070862 | A1 | 3/2005 | Tazoe et al. |
| 2005/0082300 | A1 | 4/2005 | Modrell et al. |
| 2005/0097662 | A1 | 5/2005 | Leimkuhler et al. |
| 2005/0101924 | A1 | 5/2005 | Elson et al. |
| 2005/0119630 | A1 | 6/2005 | Harvie |
| 2005/0137557 | A1 | 6/2005 | Swiecicki et al. |
| 2005/0154360 | A1 | 7/2005 | Harvie |
| 2005/0177070 | A1 | 8/2005 | Levinson et al. |
| 2005/0197639 | A1 | 9/2005 | Mombrinie |
| 2005/0197645 | A1 | 9/2005 | Karpowicz et al. |
| 2005/0273920 | A1 | 12/2005 | Marinas |
| 2005/0277904 | A1 | 12/2005 | Chase et al. |
| 2005/0279359 | A1 | 12/2005 | Leblanc et al. |
| 2006/0004332 | A1 | 1/2006 | Marx |
| 2006/0015080 | A1 | 1/2006 | Mahnensmith |
| 2006/0015081 | A1 | 1/2006 | Suzuki et al. |
| 2006/0016778 | A1 | 1/2006 | Park |
| 2006/0069359 | A1 | 3/2006 | Dipalma et al. |
| 2006/0079854 | A1 | 4/2006 | Kay et al. |
| 2006/0111648 | A1 | 5/2006 | Vermaak |
| 2006/0155214 | A1 | 7/2006 | Wightman |
| 2006/0171997 | A1 | 8/2006 | Gruenbacher et al. |
| 2006/0180566 | A1 | 8/2006 | Mataya |
| 2006/0200102 | A1 | 9/2006 | Cooper |
| 2006/0229575 | A1 | 10/2006 | Boiarski |
| 2006/0229576 | A1 | 10/2006 | Conway et al. |
| 2006/0231648 | A1 | 10/2006 | Male et al. |
| 2006/0235266 | A1 | 10/2006 | Nan |
| 2006/0235359 | A1 | 10/2006 | Marland |
| 2006/0241553 | A1 | 10/2006 | Harvie |
| 2006/0269439 | A1 | 11/2006 | White |
| 2006/0277670 | A1 | 12/2006 | Baker et al. |
| 2007/0006368 | A1 | 1/2007 | Key et al. |
| 2007/0010797 | A1 | 1/2007 | Nishtala et al. |
| 2007/0016152 | A1 | 1/2007 | Karpowicz et al. |
| 2007/0038194 | A1 | 2/2007 | Wada et al. |
| 2007/0055209 | A1 | 3/2007 | Patel et al. |
| 2007/0073252 | A1 | 3/2007 | Forgrave |
| 2007/0117880 | A1 | 5/2007 | Elson et al. |
| 2007/0118993 | A1 | 5/2007 | Bates |
| 2007/0135786 | A1 | 6/2007 | Schmidt et al. |
| 2007/0137718 | A1 | 6/2007 | Rushlander et al. |
| 2007/0149935 | A1 | 6/2007 | Dirico |
| 2007/0191804 | A1 | 8/2007 | Coley |
| 2007/0203464 | A1 | 8/2007 | Green et al. |
| 2007/0214553 | A1 | 9/2007 | Carromba et al. |
| 2007/0225663 | A1 | 9/2007 | Watt et al. |
| 2007/0225666 | A1 | 9/2007 | Otto |
| 2007/0225668 | A1 | 9/2007 | Otto |
| 2007/0266486 | A1 | 11/2007 | Ramirez |
| 2007/0282309 | A1 | 12/2007 | Bengtson et al. |
| 2008/0004576 | A1 | 1/2008 | Tanaka et al. |
| 2008/0015526 | A1 | 1/2008 | Reiner et al. |
| 2008/0015527 | A1 | 1/2008 | House |
| 2008/0033386 | A1 | 2/2008 | Okabe et al. |
| 2008/0041869 | A1 | 2/2008 | Backaert |
| 2008/0077099 | A1 | 3/2008 | House |
| 2008/0091153 | A1 | 4/2008 | Harvie |
| 2008/0091158 | A1 | 4/2008 | Yang |
| 2008/0114327 | A1 | 5/2008 | Barge |
| 2008/0167634 | A1 | 7/2008 | Kouta et al. |
| 2008/0183157 | A1 | 7/2008 | Walters |
| 2008/0215031 | A1 | 9/2008 | Belfort et al. |
| 2008/0234642 | A1 | 9/2008 | Patterson et al. |
| 2008/0269703 | A1 | 10/2008 | Collins et al. |
| 2008/0281282 | A1 | 11/2008 | Finger et al. |
| 2008/0287894 | A1 | 11/2008 | Van Den Heuvel et al. |
| 2008/0312550 | A1* | 12/2008 | Nishtala .................. A61B 5/20 600/549 |
| 2009/0025717 | A1 | 1/2009 | Pinel |
| 2009/0048570 | A1 | 2/2009 | Jensen |
| 2009/0056003 | A1 | 3/2009 | Ivie et al. |
| 2009/0069761 | A1 | 3/2009 | Vogel |
| 2009/0069765 | A1 | 3/2009 | Wortham |
| 2009/0120179 | A1 | 5/2009 | Nylander et al. |
| 2009/0192482 | A1 | 7/2009 | Dodge et al. |
| 2009/0226541 | A1 | 9/2009 | Scholz et al. |
| 2009/0234312 | A1 | 9/2009 | Otoole et al. |
| 2009/0251510 | A1 | 10/2009 | Noro et al. |
| 2009/0259206 | A1 | 10/2009 | Kai et al. |
| 2009/0264840 | A1 | 10/2009 | Virginio |
| 2009/0270822 | A1 | 10/2009 | Medeiros |
| 2009/0281510 | A1 | 11/2009 | Fisher |
| 2009/0283982 | A1 | 11/2009 | Thomas |
| 2010/0004612 | A1 | 1/2010 | Thevenin |
| 2010/0058660 | A1 | 3/2010 | Williams |
| 2010/0121289 | A1 | 5/2010 | Parks et al. |
| 2010/0158168 | A1 | 6/2010 | Murthy et al. |
| 2010/0160882 | A1 | 6/2010 | Lowe |
| 2010/0174250 | A1 | 7/2010 | Hu et al. |
| 2010/0179493 | A1 | 7/2010 | Heagle et al. |
| 2010/0185168 | A1 | 7/2010 | Graauw et al. |
| 2010/0198172 | A1 | 8/2010 | Wada et al. |
| 2010/0211032 | A1 | 8/2010 | Tsai et al. |
| 2010/0234820 | A1 | 9/2010 | Tsai et al. |
| 2010/0241104 | A1 | 9/2010 | Gilbert |
| 2010/0263113 | A1 | 10/2010 | Shelton et al. |
| 2010/0310845 | A1 | 12/2010 | Bond et al. |
| 2011/0028920 | A1 | 2/2011 | Johannison |
| 2011/0028922 | A1 | 2/2011 | Kay et al. |
| 2011/0034889 | A1 | 2/2011 | Smith |
| 2011/0036837 | A1 | 2/2011 | Shang |
| 2011/0040267 | A1 | 2/2011 | Wada et al. |
| 2011/0040271 | A1 | 2/2011 | Rogers et al. |

(56) References Cited

U.S. PATENT DOCUMENTS

| | | | |
|---|---|---|---|
| 2011/0054426 | A1 | 3/2011 | Stewart et al. |
| 2011/0060299 | A1 | 3/2011 | Wada et al. |
| 2011/0060300 | A1 | 3/2011 | Weig et al. |
| 2011/0077495 | A1 | 3/2011 | Gilbert |
| 2011/0077606 | A1 | 3/2011 | Wilcox et al. |
| 2011/0087337 | A1 | 4/2011 | Forsell |
| 2011/0137273 | A1 | 6/2011 | Muellejans et al. |
| 2011/0145993 | A1 | 6/2011 | Rader et al. |
| 2011/0152802 | A1 | 6/2011 | Dicamillo et al. |
| 2011/0164147 | A1 | 7/2011 | Takahashi et al. |
| 2011/0172620 | A1 | 7/2011 | Khambatta |
| 2011/0172625 | A1 | 7/2011 | Wada et al. |
| 2011/0202024 | A1 | 8/2011 | Cozzens |
| 2011/0238023 | A1 | 9/2011 | Slayton |
| 2011/0240648 | A1 | 10/2011 | Tucker |
| 2011/0251572 | A1 | 10/2011 | Nishtala et al. |
| 2011/0265889 | A1 | 11/2011 | Tanaka et al. |
| 2011/0276020 | A1 | 11/2011 | Mitsui |
| 2012/0029452 | A1 | 2/2012 | Roedsten |
| 2012/0035577 | A1 | 2/2012 | Tomes et al. |
| 2012/0041400 | A1 | 2/2012 | Christensen |
| 2012/0059328 | A1 | 3/2012 | Dikeman et al. |
| 2012/0066825 | A1 | 3/2012 | Birbara et al. |
| 2012/0103347 | A1 | 5/2012 | Wheaton et al. |
| 2012/0116336 | A1 | 5/2012 | Sharma et al. |
| 2012/0137420 | A1 | 6/2012 | Gordon et al. |
| 2012/0165768 | A1 | 6/2012 | Sekiyama et al. |
| 2012/0165786 | A1 | 6/2012 | Chappa et al. |
| 2012/0209216 | A1 | 8/2012 | Jensen et al. |
| 2012/0210503 | A1 | 8/2012 | Anzivino et al. |
| 2012/0233761 | A1 | 9/2012 | Huang |
| 2012/0245541 | A1 | 9/2012 | Suzuki et al. |
| 2012/0245542 | A1 | 9/2012 | Suzuki et al. |
| 2012/0245547 | A1 | 9/2012 | Wilcox et al. |
| 2012/0253303 | A1 | 10/2012 | Suzuki et al. |
| 2012/0271259 | A1 | 10/2012 | Ulert |
| 2012/0296305 | A1 | 11/2012 | Barraza Khaled et al. |
| 2012/0316522 | A1 | 12/2012 | Carter et al. |
| 2012/0330256 | A1 | 12/2012 | Wilcox et al. |
| 2013/0006206 | A1 | 1/2013 | Wada et al. |
| 2013/0045651 | A1 | 2/2013 | Esteves et al. |
| 2013/0053804 | A1 | 2/2013 | Soerensen et al. |
| 2013/0096523 | A1 | 4/2013 | Chang et al. |
| 2013/0110059 | A1 | 5/2013 | Kossow et al. |
| 2013/0138064 | A1 | 5/2013 | Stroebech et al. |
| 2013/0150813 | A1 | 6/2013 | Gordon et al. |
| 2013/0165880 | A1 | 6/2013 | Amos et al. |
| 2013/0218112 | A1 | 8/2013 | Thompson |
| 2013/0245496 | A1 | 9/2013 | Wells et al. |
| 2013/0245586 | A1 | 9/2013 | Jha |
| 2013/0292537 | A1 | 11/2013 | Dirico |
| 2013/0330501 | A1 | 12/2013 | Aizenberg et al. |
| 2014/0005647 | A1 | 1/2014 | Shuffler et al. |
| 2014/0031774 | A1 | 1/2014 | Bengtson |
| 2014/0039432 | A1 | 2/2014 | Dunbar et al. |
| 2014/0107599 | A1 | 4/2014 | Fink et al. |
| 2014/0157499 | A1 * | 6/2014 | Suzuki .................. A61G 9/006 4/144.3 |
| 2014/0171889 | A1 | 6/2014 | Hopman et al. |
| 2014/0182051 | A1 | 7/2014 | Tanimoto et al. |
| 2014/0196189 | A1 | 7/2014 | Lee et al. |
| 2014/0276501 | A1 | 9/2014 | Cisko |
| 2014/0303582 | A1 | 10/2014 | Wright et al. |
| 2014/0316381 | A1 | 10/2014 | Reglin |
| 2014/0325746 | A1 | 11/2014 | Block |
| 2014/0348139 | A1 | 11/2014 | Gomez Martinez |
| 2014/0352050 | A1 | 12/2014 | Yao et al. |
| 2014/0371628 | A1 | 12/2014 | Desai |
| 2015/0045757 | A1 | 2/2015 | Lee et al. |
| 2015/0047114 | A1 | 2/2015 | Ramirez |
| 2015/0048089 | A1 | 2/2015 | Robertson |
| 2015/0135423 | A1 | 5/2015 | Sharpe et al. |
| 2015/0157300 | A1 | 6/2015 | Ealovega et al. |
| 2015/0209188 | A1 | 7/2015 | Scheremet et al. |
| 2015/0209194 | A1 | 7/2015 | Heyman |
| 2015/0290425 | A1 | 10/2015 | Macy et al. |
| 2015/0320583 | A1 | 11/2015 | Harvie |
| 2015/0329255 | A1 | 11/2015 | Rzepecki |
| 2015/0342799 | A1 | 12/2015 | Michiels et al. |
| 2015/0359660 | A1 | 12/2015 | Harvie |
| 2015/0359996 | A1 | 12/2015 | Arora et al. |
| 2015/0366699 | A1 | 12/2015 | Nelson |
| 2016/0029998 | A1 | 2/2016 | Brister et al. |
| 2016/0030228 | A1 | 2/2016 | Jones |
| 2016/0038356 | A1 | 2/2016 | Yao et al. |
| 2016/0058322 | A1 | 3/2016 | Brister et al. |
| 2016/0060001 | A1 | 3/2016 | Wada et al. |
| 2016/0100976 | A1 | 4/2016 | Conway et al. |
| 2016/0106604 | A1 | 4/2016 | Timm |
| 2016/0113809 | A1 * | 4/2016 | Kim .................... A61G 5/1002 604/347 |
| 2016/0183689 | A1 | 6/2016 | Miner |
| 2016/0256022 | A1 | 9/2016 | Le |
| 2016/0270982 | A1 | 9/2016 | Raycheck et al. |
| 2016/0278662 | A1 | 9/2016 | Brister et al. |
| 2016/0357400 | A1 | 12/2016 | Penha et al. |
| 2016/0366699 | A1 | 12/2016 | Zhang et al. |
| 2016/0367226 | A1 | 12/2016 | Newton et al. |
| 2016/0367411 | A1 | 12/2016 | Justiz et al. |
| 2016/0367726 | A1 | 12/2016 | Gratzer |
| 2016/0374848 | A1 | 12/2016 | Sanchez et al. |
| 2017/0007438 | A1 | 1/2017 | Harvie |
| 2017/0014560 | A1 | 1/2017 | Minskoff et al. |
| 2017/0042748 | A1 | 2/2017 | Griffin |
| 2017/0100276 | A1 | 4/2017 | Joh |
| 2017/0128638 | A1 | 5/2017 | Giezendanner et al. |
| 2017/0136209 | A1 | 5/2017 | Burnett et al. |
| 2017/0143534 | A1 | 5/2017 | Sanchez |
| 2017/0165100 | A1 | 6/2017 | Jackson et al. |
| 2017/0165405 | A1 | 6/2017 | Muser et al. |
| 2017/0189225 | A1 | 7/2017 | Voorhees et al. |
| 2017/0202692 | A1 | 7/2017 | Laniado |
| 2017/0216081 | A1 | 8/2017 | Accosta |
| 2017/0238911 | A1 | 8/2017 | Duval |
| 2017/0246026 | A1 | 8/2017 | Laniado |
| 2017/0252014 | A1 | 9/2017 | Siller Gonzalez et al. |
| 2017/0252202 | A9 | 9/2017 | Sanchez et al. |
| 2017/0266031 | A1 | 9/2017 | Sanchez et al. |
| 2017/0266658 | A1 | 9/2017 | Bruno et al. |
| 2017/0281399 | A1 | 10/2017 | Vanmiddendorp et al. |
| 2017/0312116 | A1 | 11/2017 | Laniado |
| 2017/0325788 | A1 | 11/2017 | Ealovega et al. |
| 2017/0333244 | A1 | 11/2017 | Laniado |
| 2017/0348139 | A1 | 12/2017 | Newton et al. |
| 2017/0354532 | A1 | 12/2017 | Holt |
| 2017/0354551 | A1 | 12/2017 | Gawley et al. |
| 2017/0367873 | A1 | 12/2017 | Grannum |
| 2018/0002075 | A1 | 1/2018 | Lee |
| 2018/0008451 | A1 | 1/2018 | Stroebech |
| 2018/0008804 | A1 | 1/2018 | Laniado |
| 2018/0021218 | A1 | 1/2018 | Brosch et al. |
| 2018/0028349 | A1 | 2/2018 | Newton et al. |
| 2018/0037384 | A1 | 2/2018 | Archeny et al. |
| 2018/0049910 | A1 | 2/2018 | Newton |
| 2018/0064572 | A1 | 3/2018 | Wiltshire |
| 2018/0104131 | A1 | 4/2018 | Killian |
| 2018/0127187 | A1 | 5/2018 | Sewell |
| 2018/0193215 | A1 | 7/2018 | Davies et al. |
| 2018/0200101 | A1 | 7/2018 | Su |
| 2018/0228642 | A1 | 8/2018 | Davis et al. |
| 2018/0256384 | A1 | 9/2018 | Kasirye |
| 2018/0271694 | A1 | 9/2018 | Fernandez et al. |
| 2018/0317892 | A1 | 11/2018 | Catlin |
| 2018/0325748 | A1 | 11/2018 | Sharma et al. |
| 2019/0001030 | A1 | 1/2019 | Braga et al. |
| 2019/0021899 | A1 | 1/2019 | Vlet |
| 2019/0038451 | A1 | 2/2019 | Harvie |
| 2019/0046102 | A1 | 2/2019 | Kushnir et al. |
| 2019/0059938 | A1 | 2/2019 | Holsten |
| 2019/0091059 | A1 | 3/2019 | Gabriel |
| 2019/0100362 | A1 | 4/2019 | Meyers et al. |
| 2019/0133126 | A1 | 5/2019 | Modak et al. |
| 2019/0133814 | A1 | 5/2019 | Tammen et al. |
| 2019/0142624 | A1 | 5/2019 | Sanchez et al. |

(56) References Cited

U.S. PATENT DOCUMENTS

2019/0224036 A1 7/2019 Sanchez et al.
2019/0240079 A1 8/2019 Tuli
2019/0247222 A1 8/2019 Ecklund et al.
2019/0247223 A1 8/2019 Brun et al.
2019/0247623 A1 8/2019 Helm et al.
2019/0282391 A1 9/2019 Johannes et al.
2019/0314189 A1 10/2019 Acosta
2019/0314190 A1 10/2019 Sanchez et al.
2019/0321587 A1 10/2019 Mcmenamin et al.
2019/0344934 A1 11/2019 Faerber et al.
2019/0365307 A1 12/2019 Laing et al.
2019/0365561 A1 12/2019 Newton et al.
2019/0374373 A1 12/2019 Joh
2020/0008985 A1 1/2020 Nguyen et al.
2020/0016012 A1 1/2020 Dutkiewicz
2020/0030595 A1 1/2020 Boukidjian et al.
2020/0046544 A1 2/2020 Godinez et al.
2020/0055638 A1 2/2020 Lau et al.
2020/0070392 A1 3/2020 Huber et al.
2020/0085609 A1 3/2020 Schelch et al.
2020/0085610 A1 3/2020 Cohn et al.
2020/0086090 A1 3/2020 Von Weymarn-Schärli et al.
2020/0107518 A1 4/2020 Hiroshima et al.
2020/0129322 A1 4/2020 Leuckel
2020/0171217 A9 6/2020 Braga et al.
2020/0179177 A1 6/2020 Erdem et al.
2020/0187918 A1 6/2020 Wiygul
2020/0206015 A1 7/2020 Langer
2020/0206039 A1 7/2020 Mclain
2020/0214910 A1 7/2020 Varona et al.
2020/0216898 A1 7/2020 Hubbell
2020/0216989 A1 7/2020 Kinugasa et al.
2020/0229964 A1 7/2020 Staali et al.
2020/0231343 A1 7/2020 Freedman et al.
2020/0232841 A1 7/2020 Satish et al.
2020/0246172 A1 8/2020 Ho
2020/0246203 A1 8/2020 Tulk et al.
2020/0255189 A1 8/2020 Liu
2020/0261280 A1 8/2020 Heyman
2020/0276046 A1 9/2020 Staali et al.
2020/0306075 A1 10/2020 Newton et al.
2020/0315837 A1 10/2020 Radl et al.
2020/0315838 A1 10/2020 Eckert
2020/0315872 A1 10/2020 Viens et al.
2020/0315874 A1 10/2020 Viens et al.
2020/0331672 A1 10/2020 Bertram et al.
2020/0345332 A1 11/2020 Duval
2020/0353135 A1 11/2020 Gregory et al.
2020/0367677 A1 11/2020 Silsby et al.
2020/0369444 A1 11/2020 Silsby et al.
2020/0375781 A1 12/2020 Staali et al.
2020/0375810 A1 12/2020 Carlin et al.
2020/0384242 A1 12/2020 Havard et al.
2020/0385179 A1 12/2020 McCourt
2020/0390591 A1 12/2020 Glithero et al.
2020/0390592 A1 12/2020 Merrill
2020/0405521 A1 12/2020 Glasroe
2021/0008771 A1 1/2021 Huber et al.
2021/0009323 A1 1/2021 Markarian et al.
2021/0020072 A1 1/2021 Moehring et al.
2021/0023279 A1 1/2021 Radl et al.
2021/0059853 A1 3/2021 Davis et al.
2021/0061523 A1 3/2021 Bytheway
2021/0069005 A1 3/2021 Sanchez et al.
2021/0069008 A1 3/2021 Blabas et al.
2021/0069009 A1 3/2021 Im
2021/0069030 A1 3/2021 Nishikawa et al.
2021/0077993 A1 3/2021 Nazareth et al.
2021/0113749 A1 4/2021 Radl et al.
2021/0121318 A1 4/2021 Pinlac
2021/0137724 A1 5/2021 Ecklund et al.
2021/0138190 A1 5/2021 Erbey et al.
2021/0154055 A1 5/2021 Villarreal
2021/0170079 A1 6/2021 Radl et al.
2021/0178390 A1 6/2021 Oueslati et al.
2021/0186742 A1 6/2021 Newton et al.
2021/0212865 A1 7/2021 Wallajapet et al.
2021/0220162 A1 7/2021 Jamison
2021/0220163 A1 7/2021 Mayrand
2021/0228400 A1 7/2021 Glithero
2021/0228401 A1 7/2021 Becker et al.
2021/0228795 A1 7/2021 Hughett et al.
2021/0229877 A1 7/2021 Ragias et al.
2021/0236323 A1 8/2021 Austermann et al.
2021/0236324 A1 8/2021 Sweeney
2021/0251814 A1 8/2021 Jönegren et al.
2021/0267787 A1 9/2021 Nazemi
2021/0275343 A1 9/2021 Sanchez et al.
2021/0275344 A1 9/2021 Wing
2021/0290454 A1 9/2021 Yamada
2021/0315727 A1 10/2021 Jiang
2021/0353450 A1 11/2021 Sharma et al.
2021/0361469 A1 11/2021 Liu et al.
2021/0369495 A1 12/2021 Cheng et al.
2021/0386925 A1 12/2021 Hartwell et al.
2021/0393433 A1 12/2021 Godinez et al.
2022/0023091 A1 1/2022 Ecklund et al.
2022/0031523 A1 2/2022 Pierpoint
2022/0039995 A1 2/2022 Johannes et al.
2022/0047410 A1 2/2022 Walthall
2022/0062027 A1 3/2022 Mitchell et al.
2022/0062028 A1 3/2022 Mitchell et al.
2022/0062029 A1 3/2022 Johannes et al.
2022/0066825 A1 3/2022 Saraf et al.
2022/0071811 A1 3/2022 Cheng et al.
2022/0071826 A1 3/2022 Kulkarni et al.
2022/0104965 A1 4/2022 Vaninetti et al.
2022/0104976 A1 4/2022 Hoeger et al.
2022/0104981 A1 4/2022 Jones
2022/0117773 A1 4/2022 Davis et al.
2022/0117774 A1 4/2022 Meyer et al.
2022/0117775 A1 4/2022 Jones et al.
2022/0133524 A1 5/2022 Davis
2022/0151817 A1 5/2022 Mann
2022/0160949 A1 5/2022 Simiele et al.
2022/0168159 A1 6/2022 Triado et al.
2022/0193312 A1 6/2022 Lee et al.
2022/0211536 A1 7/2022 Johannes et al.
2022/0218510 A1 7/2022 Metzger et al.
2022/0229053 A1 7/2022 Levin et al.
2022/0241106 A1 8/2022 Johannes et al.
2022/0247407 A1 8/2022 Yamamoto et al.
2022/0248836 A1 8/2022 Cagle et al.
2022/0257407 A1 8/2022 Johannes et al.
2022/0265460 A1 8/2022 Coker
2022/0265462 A1 8/2022 Alder et al.
2022/0270711 A1 8/2022 Feala et al.
2022/0273482 A1 9/2022 Johannes et al.
2022/0280357 A1 9/2022 Jagannathan et al.
2022/0287689 A1 9/2022 Johannes
2022/0287867 A1 9/2022 Jones et al.
2022/0287868 A1 9/2022 Garvey et al.
2022/0296408 A1 9/2022 Evans et al.
2022/0305191 A1 9/2022 Joseph et al.
2022/0313222 A1 10/2022 Austermann et al.
2022/0313474 A1 10/2022 Kriscovich et al.
2022/0331170 A1 10/2022 Erdem et al.
2022/0339024 A1 10/2022 Johannes et al.
2022/0354685 A1 11/2022 Davis et al.
2022/0362049 A1 11/2022 Austermann et al.
2022/0370231 A1 11/2022 Wang et al.
2022/0370234 A1 11/2022 Hughett et al.
2022/0370235 A1 11/2022 Johannes et al.
2022/0370237 A1 11/2022 Parmar et al.
2022/0387001 A1 12/2022 Askenazi et al.
2022/0395390 A1 12/2022 Brooks
2022/0395391 A1 12/2022 Saunders et al.
2022/0409422 A1 12/2022 Schneider et al.
2023/0018845 A1 1/2023 Lee
2023/0020563 A1 1/2023 Sharma et al.
2023/0031640 A1 2/2023 Hughett et al.
2023/0037159 A1 2/2023 Brennan et al.
2023/0049924 A1 2/2023 Johannes et al.
2023/0052238 A1 2/2023 Oluwasogo

(56) References Cited

U.S. PATENT DOCUMENTS

| | | | |
|---|---|---|---|
| 2023/0062994 | A1 | 3/2023 | Ecklund et al. |
| 2023/0070347 | A1 | 3/2023 | Watson et al. |
| 2023/0073708 | A1 | 3/2023 | Xu et al. |
| 2023/0089032 | A1 | 3/2023 | Hughett et al. |
| 2023/0099821 | A1 | 3/2023 | Radl et al. |
| 2023/0099991 | A1 | 3/2023 | Bianchi et al. |
| 2023/0105001 | A1 | 4/2023 | Whittome et al. |
| 2023/0110577 | A1 | 4/2023 | Choi |
| 2023/0138269 | A1 | 5/2023 | Abdelal et al. |
| 2023/0145365 | A1 | 5/2023 | Martin et al. |
| 2023/0155253 | A1 | 5/2023 | Yin et al. |
| 2023/0210504 | A1 | 7/2023 | Kuroda et al. |
| 2023/0210685 | A1 | 7/2023 | Fallows et al. |
| 2023/0218426 | A1 | 7/2023 | Hughett |
| 2023/0240884 | A1 | 8/2023 | Davis et al. |
| 2023/0248562 | A1 | 8/2023 | Sanchez et al. |
| 2023/0248564 | A1 | 8/2023 | Mann et al. |
| 2023/0255812 | A1 | 8/2023 | Sanchez et al. |
| 2023/0255813 | A1 | 8/2023 | Sanchez et al. |
| 2023/0255815 | A1 | 8/2023 | Newton |
| 2023/0263650 | A1 | 8/2023 | Sanchez et al. |
| 2023/0263655 | A1 | 8/2023 | Johannes et al. |
| 2023/0277362 | A1 | 9/2023 | Davis et al. |
| 2023/0285178 | A1 | 9/2023 | Sanchez et al. |
| 2023/0293339 | A1 | 9/2023 | James |
| 2023/0301846 | A1 | 9/2023 | Greenwood |
| 2023/0355423 | A1 | 11/2023 | Stevenson et al. |
| 2023/0404791 | A1 | 12/2023 | Ecklund et al. |
| 2024/0008444 | A1 | 1/2024 | Su et al. |
| 2024/0009023 | A1 | 1/2024 | Johannes et al. |
| 2024/0024170 | A1 | 1/2024 | Scott |
| 2024/0041638 | A1 | 2/2024 | Johannes et al. |
| 2024/0058161 | A1 | 2/2024 | Ulreich et al. |
| 2024/0065881 | A1 | 2/2024 | Kuroda et al. |
| 2024/0099874 | A1 | 3/2024 | Sanchez et al. |
| 2024/0110318 | A1 | 4/2024 | Bendt et al. |
| 2024/0123134 | A1 | 4/2024 | Kharkar et al. |
| 2024/0148539 | A1 | 5/2024 | Austermann et al. |
| 2024/0261131 | A1 | 8/2024 | Garvey et al. |
| 2025/0009552 | A1 | 1/2025 | Blabas et al. |

FOREIGN PATENT DOCUMENTS

| | | | |
|---|---|---|---|
| CA | 2165286 | C | 9/1999 |
| CA | 2354132 | A1 | 6/2000 |
| CA | 2359091 | C | 9/2003 |
| CA | 2488867 | C | 8/2007 |
| CA | 3050918 | A1 | 8/2018 |
| CA | 3098571 | A1 | 11/2019 |
| CN | 2269203 | Y | 12/1997 |
| CN | 1332620 | A | 1/2002 |
| CN | 1434693 | A | 8/2003 |
| CN | 1533755 | A | 10/2004 |
| CN | 1602825 | A | 4/2005 |
| CN | 1720888 | A | 1/2006 |
| CN | 2936204 | Y | 8/2007 |
| CN | 101262836 | A | 9/2008 |
| CN | 101522148 | A | 9/2009 |
| CN | 102159159 | A | 8/2011 |
| CN | 202184840 | U | 4/2012 |
| CN | 102481441 | A | 5/2012 |
| CN | 202463712 | U | 10/2012 |
| CN | 202950810 | U | 5/2013 |
| CN | 103533968 | A | 1/2014 |
| CN | 103717180 | A | 4/2014 |
| CN | 204562697 | U | 8/2015 |
| CN | 105411783 | A | 3/2016 |
| CN | 105451693 | A | 3/2016 |
| CN | 105534632 | A | 5/2016 |
| CN | 106132360 | A | 11/2016 |
| CN | 205849719 | U | 1/2017 |
| CN | 205924282 | U | 2/2017 |
| CN | 106726089 | A | 5/2017 |
| CN | 107847384 | A | 3/2018 |
| CN | 107920912 | A | 4/2018 |
| CN | 108420590 | A | 8/2018 |
| CN | 209285902 | U | 8/2019 |
| CN | 110381883 | A | 10/2019 |
| CN | 211198839 | U | 8/2020 |
| CN | 111991136 | A | 11/2020 |
| CN | 112022488 | A | 12/2020 |
| CN | 212234893 | U | 12/2020 |
| CN | 212466312 | U | 2/2021 |
| CN | 112566550 | A | 3/2021 |
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |
| DE | 79818 | C | 10/1893 |
| DE | 1516466 | A1 | 6/1969 |
| DE | 2721330 | A1 | 11/1977 |
| DE | 2742298 | A1 | 3/1978 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 102005037762 | B3 | 9/2006 |
| DE | 102011103783 | A1 | 12/2012 |
| DE | 102012112818 | A1 | 6/2014 |
| DE | 202015104597 | U1 | 7/2016 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0610638 | A1 | 8/1994 |
| EP | 0613355 | A1 | 9/1994 |
| EP | 0613355 | B1 | 1/1997 |
| EP | 0787472 | A1 | 8/1997 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3569205 | B1 | 6/2023 |
| EP | 4382082 | A2 | 6/2024 |
| EP | 4445881 | A2 | 10/2024 |
| EP | 4464288 | A2 | 11/2024 |
| GB | 871820 | A | 7/1961 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |

(56) References Cited

FOREIGN PATENT DOCUMENTS

| | | | |
|---|---|---|---|
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58188016 | U | 12/1983 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H05123349 | A | 5/1993 |
| JP | H05123350 | A | 5/1993 |
| JP | H0626264 | U | 4/1994 |
| JP | 3087938 | B2 | 10/1995 |
| JP | H085630 | A | 1/1996 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003528691 | A | 9/2003 |
| JP | 2004057578 | A | 2/2004 |
| JP | 2004130056 | A | 4/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011218130 | A | 11/2011 |
| JP | 2011224070 | A | 11/2011 |
| JP | 3175719 | U | 4/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 2017512603 | A | 5/2017 |
| JP | 2017201272 | A | 11/2017 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020520775 | A | 7/2020 |
| JP | 2021007472 | A | 1/2021 |
| JP | 2021120686 | A | 8/2021 |
| JP | 2021522009 | A | 8/2021 |
| JP | 2021522013 | A | 8/2021 |
| JP | 7129493 | B2 | 8/2022 |
| JP | 2023532132 | A | 7/2023 |
| KR | 200290061 | Y1 | 9/2002 |
| KR | 20030047451 | A | 6/2003 |
| KR | 20080005516 | A | 1/2008 |
| KR | 20090104426 | A | 10/2009 |
| KR | 20090110359 | A | 10/2009 |
| KR | 20120005922 | A | 1/2012 |
| KR | 20140039485 | A | 4/2014 |
| KR | 101432639 | B1 | 8/2014 |
| KR | 20180106659 | A | 10/2018 |
| KR | 20180108774 | A | 10/2018 |
| PT | 2068717 | E | 6/2013 |
| SE | 505542 | C2 | 9/1997 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9303690 | A1 | 3/1993 |
| WO | 9307839 | A1 | 4/1993 |
| WO | 9309736 | A2 | 5/1993 |
| WO | 9309736 | A3 | 6/1993 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005051252 | A1 | 6/2005 |

(56) References Cited

FOREIGN PATENT DOCUMENTS

| | | | |
|---|---|---|---|
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007134608 | A2 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012020506 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018235026 | A1 | 12/2018 |
| WO | 2018235065 | A1 | 12/2018 |
| WO | 2019004404 | A1 | 1/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |

(56) References Cited

FOREIGN PATENT DOCUMENTS

| | | | |
|---|---|---|---|
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049175 | A1 | 3/2023 |
| WO | 2023086394 | A1 | 5/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023191764 | A1 | 10/2023 |
| WO | 2023244238 | A1 | 12/2023 |
| WO | 2024058788 | A1 | 3/2024 |
| WO | 2024253655 | A1 | 12/2024 |

OTHER PUBLICATIONS

Wikipedia, Decibel (Year: 2020).*
Wikipedia, Fiberglass (Year: 2020).*
U.S. Appl. No. 14/433,773 filed Apr. 3, 2020.
U.S. App. No. 63/064,126 filed Aug. 11, 2020.
U.S. Appl. No. 17/664,914, filed May 25, 2022.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Feb. 15, 2023.
Advisory Action for U.S. Appl. No. 16/452,258 mailed Oct. 26, 2022.
Advisory Action for U.S. Appl. No. 17/450,864 mailed on Mar. 21, 2024.
Advisory Action for U.S. Appl. No. 17/662,700 mailed Jan. 30, 2023.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 16/478,180 mailed May 31, 2023.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/444,792 mailed Jun. 15, 2023.
Final Office Action for U.S. Appl. No. 17/448,811 mailed Aug. 3, 2023.
Final Office Action for U.S. Appl. No. 17/451,345 mailed May 3, 2023.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015781 mailed May 6, 2022.
International Search Report and Written Opinion from International Application No. PCT/US2022/018159 mailed Dec. 12, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.

(56) References Cited

OTHER PUBLICATIONS

International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
Issue Notification for U.S. Appl. No. 16/899,956 mailed Mar. 29, 2023.
Issue Notification for U.S. Appl. No. 16/905,400 mailed Nov. 30, 2022.
Non-Final Office Action for U.S. Appl. No. 16/433,773 mailed Apr. 11, 2023.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,258 mailed Apr. 26, 2023.
Non-Final Office Action for U.S. Appl. No. 16/478,180 mailed Dec. 20, 2022.
Non-Final Office Action for U.S. Appl. No. 16/904,868 mailed Mar. 15, 2023.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,550 mailed Oct. 24, 2023.
Non-Final Office Action for U.S. Appl. No. 17/051,585 mailed Mar. 29, 2023.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/446,256 mailed Apr. 13, 2023.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/501,591 mailed Apr. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/655,464 mailed Mar. 14, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 18/139,523 mailed Aug. 17, 2023.
Notice of Allowance for U.S. Appl. No. 16/245,726 mailed Jul. 6, 2023.
Notice of Allowance for U.S. Appl. No. 16/449,039 mailed Dec. 15, 2022.
Notice of Allowance for U.S. Appl. No. 16/899,956 mailed Dec. 1, 2022.
Notice of Allowance for U.S. Appl. No. 17/051,554 mailed Jul. 6, 2023.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/663,046 mailed Jan. 30, 2023.
Notice of Allowance for U.S. Appl. No. 18/299,788 mailed Jul. 24, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Text Messages to Lorena Eckert Re Prototype PureWick Holder dated Apr. 16, 2022.
U.S. Appl. No. 15/260,103 filed Sep. 8, 2016.
U.S. Appl. No. 15/612,325 filed Jun. 2, 2017.
U.S. Appl. No. 17/664,487 filed May 23, 2022.
U.S. Appl. No. 17/996,064 filed Oct. 12, 2022.
U.S. Appl. No. 17/996,155 filed Oct. 13, 2022.
U.S. Appl. No. 17/996,253 filed Oct. 14, 2022.
U.S. Appl. No. 17/996,468 filed Oct. 18, 2022.
U.S. Appl. No. 17/996,556 filed Oct. 19, 2022.
U.S. Appl. No. 18/003,029 filed Dec. 22, 2022.
U.S. Appl. No. 18/006,807 filed Jan. 25, 2023.
U.S. Appl. No. 18/007,105 filed Jan. 27, 2023.
U.S. Appl. No. 18/041,109 filed Feb. 9, 2023.
U.S. Appl. No. 18/042,842 filed Feb. 24, 2023.
U.S. Appl. No. 18/043,618 filed Mar. 1, 2023.
U.S. Appl. No. 18/115,444 filed Feb. 28, 2023.
U.S. Appl. No. 18/134,857 filed Apr. 14, 2023.
U.S. Appl. No. 18/140,163 filed Apr. 27, 2023.
U.S. Appl. No. 18/140,751 filed Apr. 28, 2023.
U.S. Appl. No. 18/164,800 filed Feb. 6, 2023.

(56) References Cited

OTHER PUBLICATIONS

U.S. Appl. No. 18/198,464 filed May 17, 2023.
U.S. Appl. No. 18/246,121 filed Mar. 21, 2023.
U.S. Appl. No. 18/247,986 filed Apr. 5, 2023.
U.S. Appl. No. 18/259,626 filed Jun. 28, 2023.
U.S. Appl. No. 18/260,122 filed Jun. 30, 2023.
U.S. Appl. No. 18/260,391 filed Jul. 5, 2023.
U.S. Appl. No. 18/260,394 filed Jul. 5, 2023.
U.S. Appl. No. 18/263,800 filed Aug. 1, 2023.
U.S. Appl. No. 18/264,004 filed Aug. 2, 2023.
U.S. Appl. No. 18/265,736 filed Jun. 7, 2023.
U.S. Appl. No. 18/299,788 filed Apr. 13, 2023.
U.S. Appl. No. 18/335,579 filed Jun. 15, 2023.
U.S. Appl. No. 18/548,152 filed Aug. 28, 2023.
U.S. Appl. No. 63/150,640 filed Feb. 18, 2021.
U.S. Appl. No. 63/308,190 filed Feb. 9, 2022.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Merriam-Webster Dictionary, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, Mar./Apr. 1993, pp. 51-55.
Vinas,"A Solution For An Awkward—But Serious—Subject", http://www.aero-news.net/index.cfm?do=main.textpost&id=69ae2bb1-838b-4098-a7b5-7flbb2505688 last accessed Feb. 8, 2021.
Wikipedia Article,"Zylinder (Geometrie)", 284 https://de.wikipedia.org/w/index.php?title=Zylinder (Geometrie)&oldid=154862081, version of Jun. 1, 2016, 7 pages.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Feb. 16, 2022.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/452,145 mailed Mar. 25, 2022.
Final Office Action for U.S. Appl. No. 16/899,956 mailed Apr. 19, 2021.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.

(56) References Cited

OTHER PUBLICATIONS

International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/012794 mailed May 3, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Oct. 22, 2021.

(56) References Cited

OTHER PUBLICATIONS

Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/899,956 mailed Dec. 29, 2021.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Nov. 26, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice of Allowance for U.S. Appl. No. 29/741,751 mailed Jun. 9, 2022.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
U.S. Appl. No. 14/625,469 filed Feb. 28, 2015.
U.S. Appl. No. 14/947,759 filed Nov. 20, 2015.
U.S. Appl. No. 14/952,591 filed Nov. 25, 2015.
U.S. Appl. No. 15/171,968 filed Jun. 2, 2016.
U.S. Appl. No. 15/221,106 filed Jul. 27, 2016.
U.S. Appl. No. 15/384,196 filed Dec. 19, 2016.
U.S. Appl. No. 16/245,726 filed Jan. 11, 2019.
U.S. Appl. No. 16/369,676 filed Mar. 29, 2019.
U.S. Appl. No. 16/433,773 filed Jun. 6, 2019.
U.S. Appl. No. 16/449,039 filed Jun. 21, 2019.
U.S. Appl. No. 16/452,145 filed Jun. 25, 2019.
U.S. Appl. No. 16/452,258 filed Jun. 25, 2019.
U.S. Appl. No. 16/478,180 filed Jul. 16, 2019.
U.S. Appl. No. 16/904,868 filed Jun. 18, 2020.
U.S. Appl. No. 16/905,400 filed Jun. 18, 2020.
U.S. Appl. No. 17/051,550 filed Oct. 29, 2020.
U.S. Appl. No. 17/051,554 filed Oct. 29, 2020.
U.S. Appl. No. 17/051,585 filed Oct. 29, 2020.
U.S. Appl. No. 17/051,600 filed Oct. 29, 2020.
U.S. Appl. No. 17/088,272 filed Nov. 3, 2020.
U.S. Appl. No. 17/179,116 filed Feb. 18, 2021.
U.S. Appl. No. 17/330,657 filed May 26, 2021.
U.S. Appl. No. 17/378,015 filed Jul. 16, 2021.
U.S. Appl. No. 17/394,055 filed Aug. 4, 2021.
U.S. Appl. No. 17/412,864 filed Aug. 26, 2021.
U.S. Appl. No. 17/444,825 filed Aug. 10, 2021.
U.S. Appl. No. 17/446,256 filed Aug. 27, 2021.
U.S. Appl. No. 17/446,654 filed Sep. 1, 2021.
U.S. Appl. No. 17/447,123 filed Sep. 8, 2021.
U.S. Appl. No. 17/450,864 filed Oct. 14, 2021.
U.S. Appl. No. 17/451,345 filed Oct. 19, 2021.
U.S. Appl. No. 17/451,354 filed Oct. 19, 2021.
U.S. Appl. No. 17/453,260 filed Nov. 2, 2021.
U.S. Appl. No. 17/453,560 filed Nov. 4, 2021.
U.S. Appl. No. 17/461,036 mailed Aug. 30, 2021.
U.S. Appl. No. 17/494,578 filed Oct. 5, 2021.
U.S. Appl. No. 17/501,591 filed Oct. 14, 2021.
U.S. Appl. No. 17/595,747 filed Nov. 23, 2021.
U.S. Appl. No. 17/597,408 filed Jan. 5, 2022.
U.S. Appl. No. 17/597,673 filed Jan. 18, 2022.
U.S. Appl. No. 17/614,173 filed Nov. 24, 2021.
U.S. Appl. No. 17/631,619 filed Jan. 31, 2022.
U.S. Appl. No. 17/645,821 filed Dec. 23, 2021.
U.S. Appl. No. 17/646,771 filed Jan. 3, 2022.
U.S. Appl. No. 17/653,314 filed Mar. 3, 2022.
U.S. Appl. No. 17/653,920 filed Mar. 8, 2022.
U.S. Appl. No. 17/657,474 filed Mar. 31, 2022.
U.S. Appl. No. 17/661,090 filed Apr. 28, 2022.
U.S. Appl. No. 17/662,700 filed May 10, 2022.
U.S. Appl. No. 17/663,046 filed May 12, 2022.
U.S. Appl. No. 17/664,914 filed May 25, 222.
U.S. Appl. No. 17/749,340 filed May 20, 2022.
U.S. Appl. No. 17/754,736 filed Apr. 11, 2022.
U.S. Appl. No. 17/756,201 filed May 19, 2022.
U.S. Appl. No. 29/741,751 filed Jul. 15, 2020.
U.S. Appl. No. 61/955,537 filed Mar. 19, 2014.
U.S. Appl. No. 62/082,279 filed Nov. 20, 2014.
U.S. Appl. No. 62/084,078 filed Nov. 25, 2014.
U.S. Appl. No. 62/414,963 filed Oct. 31, 2016.
U.S. Appl. No. 62/452,437 filed Jan. 31, 2017.
U.S. Appl. No. 62/485,578 filed Apr. 14, 2017.
U.S. Appl. No. 62/665,297 filed May 1, 2018.
U.S. Appl. No. 62/665,302 filed May 1, 2018.
U.S. Appl. No. 62/665,317 filed May 1, 2018.
U.S. Appl. No. 62/665,321 filed May 1, 2018.
U.S. Appl. No. 62/665,331 filed May 1, 2018.
U.S. Appl. No. 62/665,335 filed May 1, 2018.

(56) References Cited

OTHER PUBLICATIONS

U.S. Appl. No. 62/853,279 filed May 28, 2019.
U.S. Appl. No. 62/853,889 filed May 29, 2019.
U.S. Appl. No. 62/864,656 filed Jun. 21, 2019.
U.S. Appl. No. 62/873,045 filed Jul. 11, 2019.
U.S. Appl. No. 62/873,048 filed Jul. 11, 2019.
U.S. Appl. No. 62/876,500 filed Jul. 19, 2019.
U.S. Appl. No. 62/877,558 filed Jul. 23, 2019.
U.S. Appl. No. 62/883,172 filed Aug. 6, 2019.
U.S. Appl. No. 62/889,149 filed Aug. 20, 2019.
U.S. Appl. No. 62/923,279 filed Oct. 18, 2019.
U.S. Appl. No. 62/926,767 filed Oct. 28, 2019.
U.S. Appl. No. 62/935,337 filed Nov. 14, 2019.
U.S. Appl. No. 62/938,447 filed Nov. 21, 2019.
U.S. Appl. No. 62/949,187 filed Dec. 17, 2019.
U.S. Appl. No. 62/956,756 filed Jan. 3, 2020.
U.S. Appl. No. 62/956,767 filed Jan. 3, 2020.
U.S. Appl. No. 62/956,770 filed Jan. 3, 2020.
U.S. Appl. No. 62/967,977 filed Jan. 30, 2020.
U.S. Appl. No. 62/994,912 filed Mar. 26, 2020.
U.S. Appl. No. 63/008,112 filed Apr. 10, 2020.
U.S. Appl. No. 63/011,445 filed Apr. 17, 2020.
U.S. Appl. No. 63/011,487 filed Apr. 17, 2020.
U.S. Appl. No. 63/011,571 filed Apr. 17, 2020.
U.S. Appl. No. 63/011,657 filed Apr. 17, 2020.
U.S. Appl. No. 63/011,760 filed Apr. 17, 2020.
U.S. Appl. No. 63/012,347 filed Apr. 20, 2020.
U.S. Appl. No. 63/012,384 filed Apr. 20, 2020.
U.S. Appl. No. 63/030,685 filed May 27, 2020.
U.S. Appl. No. 63/033,310 filed Jun. 2, 2020.
U.S. Appl. No. 63/047,374 filed Jul. 2, 2020.
U.S. Appl. No. 63/061,241 filed Aug. 5, 2020.
U.S. Appl. No. 63/061,244 filed Aug. 5, 2020.
U.S. Appl. No. 63/061,834 filed Aug. 6, 2020.
U.S. Appl. No. 63/064,017 filed Aug. 11, 2020.
U.S. Appl. No. 63/064,126 filed Aug. 11, 2020.
U.S. Appl. No. 63/067,542 filed Aug. 19, 2020.
U.S. Appl. No. 63/071,438 filed Aug. 28, 2020.
U.S. Appl. No. 63/071,821 filed Aug. 28, 2020.
U.S. Appl. No. 63/073,545 filed Sep. 2, 2020.
U.S. Appl. No. 63/073,553 filed Sep. 2, 2020.
U.S. Appl. No. 63/074,051 filed Sep. 3, 2020.
U.S. Appl. No. 63/074,066 filed Sep. 3, 2020.
U.S. Appl. No. 63/076,032 filed Sep. 9, 2020.
U.S. Appl. No. 63/076,474 filed Sep. 10, 2020.
U.S. Appl. No. 63/076,477 filed Sep. 10, 2020.
U.S. Appl. No. 63/082,261 filed Sep. 23, 2020.
U.S. Appl. No. 63/088,506 filed Oct. 7, 2020.
U.S. Appl. No. 63/088,511 filed Oct. 7, 2020.
U.S. Appl. No. 63/088,539 filed Oct. 7, 2020.
U.S. Appl. No. 63/094,464 filed Oct. 21, 2020.
U.S. Appl. No. 63/094,498 filed Oct. 21, 2020.
U.S. Appl. No. 63/094,594 filed Oct. 21, 2020.
U.S. Appl. No. 63/094,608 filed Oct. 21, 2020.
U.S. Appl. No. 63/094,626 filed Oct. 21, 2020.
U.S. Appl. No. 63/109,066 filed Nov. 3, 2020.
U.S. Appl. No. 63/109,084 filed Nov. 3, 2020.
U.S. Appl. No. 63/112,417 filed Nov. 11, 2020.
U.S. Appl. No. 63/119,161 filed Nov. 30, 2020.
U.S. Appl. No. 63/124,271 filed Dec. 11, 2020.
U.S. Appl. No. 63/133,892 filed Jan. 5, 2021.
U.S. Appl. No. 63/134,287 filed Jan. 6, 2021.
U.S. Appl. No. 63/134,450 filed Jan. 6, 2021.
U.S. Appl. No. 63/134,631 filed Jan. 7, 2021.
U.S. Appl. No. 63/134,632 filed Jan. 7, 2021.
U.S. Appl. No. 63/134,754 filed Jan. 7, 2021.
U.S. Appl. No. 63/138,878 filed Jan. 19, 2021.
U.S. Appl. No. 63/146,946 filed Feb. 8, 2021.
U.S. Appl. No. 63/147,013 filed Feb. 8, 2021.
U.S. Appl. No. 63/147,299 filed Feb. 9, 2021.
U.S. Appl. No. 63/148,723 filed Feb. 12, 2021.
U.S. Appl. No. 63/154,248 filed Feb. 26, 2021.
U.S. Appl. No. 63/155,395 filed Mar. 2, 2021.
U.S. Appl. No. 63/157,007 filed Mar. 5, 2021.
U.S. Appl. No. 63/157,014 filed Mar. 5, 2021.
U.S. Appl. No. 63/159,142 filed Mar. 10, 2021.
U.S. Appl. No. 63/159,186 filed Mar. 10, 2021.
U.S. Appl. No. 63/159,210 filed Mar. 10, 2021.
U.S. Appl. No. 63/159,280 filed Mar. 10, 2021.
U.S. Appl. No. 63/165,273 filed Mar. 24, 2021.
U.S. Appl. No. 63/165,384 filed Mar. 24, 2021.
U.S. Appl. No. 63/171,165 filed Apr. 6, 2021.
U.S. Appl. No. 63/172,975 filed Apr. 9, 2021.
U.S. Appl. No. 63/181,695 filed Apr. 29, 2021.
U.S. Appl. No. 63/191,558 filed May 21, 2021.
U.S. Appl. No. 63/192,274 filed May 24, 2021.
U.S. Appl. No. 63/192,289 filed May 24, 2021.
U.S. Appl. No. 63/193,235 filed May 26, 2021.
U.S. Appl. No. 63/193,406 filed May 26, 2021.
U.S. Appl. No. 63/193,891 filed May 27, 2021.
U.S. Appl. No. 63/208,262 filed Jun. 8, 2021.
U.S. Appl. No. 63/214,551 filed Jun. 24, 2021.
U.S. Appl. No. 63/214,570 filed Jun. 24, 2021.
U.S. Appl. No. 63/215,017 filed Jun. 25, 2021.
U.S. Appl. No. 63/228,244 filed Aug. 2, 2021.
U.S. Appl. No. 63/228,252 filed Aug. 2, 2021.
U.S. Appl. No. 63/228,258 filed Aug. 2, 2021.
U.S. Appl. No. 63/230,894 filed Aug. 9, 2021.
U.S. Appl. No. 63/230,897 filed Aug. 9, 2021.
U.S. Appl. No. 63/238,457 filed Aug. 30, 2021.
U.S. Appl. No. 63/238,477 filed Aug. 30, 2021.
U.S. Appl. No. 63/241,562 filed Sep. 8, 2021.
U.S. Appl. No. 63/241,564 filed Sep. 8, 2021.
U.S. Appl. No. 63/241,575 filed Sep. 8, 2021.
U.S. Appl. No. 63/246,972 filed Sep. 22, 2021.
U.S. Appl. No. 63/247,375 filed Sep. 23, 2021.
U.S. Appl. No. 63/247,478 filed Sep. 23, 2021.
U.S. Appl. No. 63/247,491 filed Sep. 23, 2021.
U.S. Appl. No. 63/299,208 filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims To Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.

(56) References Cited

OTHER PUBLICATIONS

"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/US/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee , et al., "Continuous Fabrication of Wide-Tip Microstructures for Bio-Inspired Dry Adhesives via Tip Inking Process", Journal of Chemistry, Jan. 2, 2019, pp. 1-5.
MacAulay , et al., "A Noninvasive Continence Management System: Development and Evaluation of a Novel Toileting Device for Women", The Wound, Ostomy and Continence Nurses Society, 2007, pp. 641-648.
Newman , et al., "The Urinary Incontinence Sourcebook", Petition for Interparties Review, 1997, 23 pages.
Newton , et al., "Measuring Safety, Effectiveness and Ease of Use of PureWick in the Management of Urinary Incontinence in Bedbound Women: Case Studies", Jan. 8, 2016, 11 pages.
Parmar , "10 Finalists Chosen for Dare-to-Dream Medtech Design Challenge (PureWick)", Design Services, Nov. 10, 2014, 3 pages.
Parness , et al., "A microfabricated wedge-shaped adhesive array displaying gecko-like dynamic adhesion, directionality", J.R. Soc. Interface, 2009, pp. 1223-1232.
Purewick , "Incontinence Relief for Women", Presentation, Sep. 23, 2015, 7 pages.
Pytlik , "Super Absorbent Polymers", University of Buffalo.
Sachtman , "New Relief for Pilots? It Depends", Wired, 2008, 2 pages.
Tsipenyuk , et al., "Use of biomimetic hexagonal surface texture in friction against lubricated skin", Journal of The Royal Society—Interface, 2014, pp. 1-6.
Advisory Action for U.S. Appl. No. 16/478,180 mailed Sep. 21, 2022.
Advisory Action for U.S. Appl. No. 16/904,868 mailed Jun. 15, 2022.
Final Office Action for U.S. Appl. No. 16/449,039 mailed Aug. 1, 2022.
Final Office Action for U.S. Appl. No. 16/452,258 mailed Jun. 14, 2022.
Final Office Action for U.S. Appl. No. 16/478,180 mailed Jun. 22, 2022.
International Search Report and Written Opinion from International Application No. PCT/US2021/039866 mailed Oct. 7, 2021.
International Search Report and Written Opinion from International Application No. PCT/US2021/055515 mailed Jan. 28, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/015492 mailed Apr. 26, 2022.
International Search Report and Written Opinion from International Application No. PCT/US2022/016942 mailed Jun. 8, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
Issue Notification for U.S. Appl. No. 17/088,272 mailed Jun. 15, 2022.
Issue Notification for U.S. Appl. No. 17/330,657 mailed Jun. 22, 2022.

(56) References Cited

OTHER PUBLICATIONS

Non-Final Office Action for U.S. Appl. No. 17/662,700 mailed Jul. 22, 2022.
Notice of Allowance for U.S. Appl. No. 16/899,956 mailed Aug. 10, 2022.
Notice of Allowance for U.S. Appl. No. 16/905,400 mailed Aug. 17, 2022.
U.S. Appl. No. 17/758,152 filed Jun. 29, 2022.
U.S. Appl. No. 17/758,316 filed Jul. 1, 2022.
U.S. Appl. No. 17/759,697 filed Jul. 28, 2022.
U.S. Appl. No. 17/878,268 filed Aug. 1, 2022.
U.S. Appl. No. 17/907,125 filed Sep. 23, 2022.
U.S. Appl. No. 17/912,147 filed Sep. 16, 2022.
U.S. Appl. No. 17/929,887 filed Sep. 6, 2022.
U.S. Appl. No. 17/930,238 filed Sep. 7, 2022.
U.S. Appl. No. 17/933,590 filed Sep. 20, 2022.
U.S. Appl. No. 62/967,158 filed Jan. 26, 2020.
U.S. Appl. No. 62/991,754 filed Mar. 19, 2020.
U.S. Appl. No. 63/241,328 filed Sep. 7, 2021.
Advisory Action for U.S. Appl. No. 16/433,773 mailed Dec. 29, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/446,654 mailed Apr. 15, 2024.
Advisory Action for U.S. Appl. No. 17/448,811 mailed Nov. 15, 2023.
Advisory Action for U.S. Appl. No. 17/450,864 mailed Mar. 21, 2024.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 16/369,676 mailed Aug. 31, 2023.
Final Office Action for U.S. Appl. No. 16/433,773 mailed Oct. 10, 2023.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/179,116 mailed Oct. 31, 2023.
Final Office Action for U.S. Appl. No. 17/444,792 mailed Apr. 3, 2024.
Final Office Action for U.S. Appl. No. 17/446,256 mailed Sep. 19, 2023.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/450,864 mailed Dec. 28, 2023.
Final Office Action for U.S. Appl. No. 17/451,345 mailed Apr. 18, 2024.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 17/808,354 mailed Apr. 10, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Dec. 6, 2023.
Issue Notification for U.S. Appl. No. 17/461,036 mailed Oct. 11, 2023.
Issue Notification for U.S. Appl. No. 17/657,474 mailed Jun. 19, 2024.

(56) References Cited

OTHER PUBLICATIONS

Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/452,145 mailed Nov. 2, 2023.
Non-Final Office Action for U.S. Appl. No. 16/452,258 mailed Jun. 20, 2024.
Non-Final Office Action for U.S. Appl. No. 16/478,180 mailed Nov. 7, 2023.
Non-Final Office Action for U.S. Appl. No. 16/904,868 mailed Mar. 12, 2024.
Non-Final Office Action for U.S. Appl. No. 17/051,550 mailed Oct. 2, 2023.
Non-Final Office Action for U.S. Appl. No. 17/051,585 mailed Jan. 8, 2024.
Non-Final Office Action for U.S. Appl. No. 17/051,600 mailed Jan. 17, 2024.
Non-Final Office Action for U.S. Appl. No. 17/179,116 mailed Feb. 2, 2024.
International Search Report and Written Opinion from International Application No. PCT/US2023/018474 mailed Sep. 11, 2023.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/077208 mailed May 10, 2024.
Issue Notification for U.S. Appl. No. 16/245,726 mailed Oct. 18, 2023.
Issue Notification for U.S. Appl. No. 16/449,039 mailed Jun. 19, 2024.
Issue Notification for U.S. Appl. No. 17/051,550 mailed Mar. 13, 2024.
Issue Notification for U.S. Appl. No. 17/051,554 mailed Mar. 6, 2024.
Non-Final Office Action for U.S. Appl. No. 17/444,792 mailed Nov. 17, 2023.
Non-Final Office Action for U.S. Appl. No. 17/446,256 mailed Feb. 13, 2024.
Non-Final Office Action for U.S. Appl. No. 17/446,654 mailed Sep. 8, 2023.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/450,864 mailed May 29, 2024.
Non-Final Office Action for U.S. Appl. No. 17/451,345 mailed Jan. 17, 2024.
Non-Final Office Action for U.S. Appl. No. 17/451,354 mailed Apr. 4, 2024.
Non-Final Office Action for U.S. Appl. No. 17/453,560 mailed Oct. 16, 2023.
Non-Final Office Action for U.S. Appl. No. 17/595,747 mailed Jun. 7, 2024.
Non-Final Office Action for U.S. Appl. No. 17/597,673 mailed Mar. 20, 2024.
Non-Final Office Action for U.S. Appl. No. 17/645,821 mailed Oct. 25, 2023.
Non-Final Office Action for U.S. Appl. No. 17/646,771 mailed Apr. 24, 2024.
Non-Final Office Action for U.S. Appl. No. 17/653,137 mailed Jan. 18, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/657,474 mailed Sep. 12, 2023.
Non-Final Office Action for U.S. Appl. No. 17/661,090 mailed May 22, 2024.
Non-Final Office Action for U.S. Appl. No. 17/664,487 mailed Jun. 17, 2024.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/134,857 mailed Jan. 25, 2024.
Non-Final Office Action for U.S. Appl. No. 18/140,163 mailed Nov. 9, 2023.
Non-Final Office Action for U.S. Appl. No. 18/140,751 mailed Jun. 21, 2024.
Non-Final Office Action for U.S. Appl. No. 18/140,751 mailed Sep. 14, 2023.
Non-Final Office Action for U.S. Appl. No. 18/164,800 mailed Mar. 22, 2024.
Non-Final Office Action for U.S. Appl. No. 18/198,464 mailed Dec. 7, 2023.
Non-Final Office Action for U.S. Appl. No. 18/389,009 mailed May 24, 2024.
Notice of Allowance for U.S. Appl. No. 16/369,676 mailed Jun. 17, 2024.
Notice of Allowance for U.S. Appl. No. 16/369,676 mailed Nov. 14, 2023.
Notice of Allowance for U.S. Appl. No. 16/449,039 mailed Mar. 28, 2024.
Notice of Allowance for U.S. Appl. No. 17/051,550 mailed Feb. 7, 2024.
Notice of Allowance for U.S. Appl. No. 17/051,554 mailed Oct. 18, 2023.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 18/198,464 mailed Apr. 17, 2024.
Notice of Allowance for U.S. Appl. No. 18/299,788 mailed Nov. 6, 2023.

(56) References Cited

OTHER PUBLICATIONS

Restriction Requirement for U.S. Appl. No. 17/051,600 mailed Sep. 21, 2023.
Restriction Requirement for U.S. Appl. No. 17/527,769 mailed Jun. 17, 2024.
Restriction Requirement for U.S. Appl. No. 17/667,097 mailed Mar. 20, 2024.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/444,792 filed Aug. 10, 2021.
U.S. Appl. No. 17/451,719 filed Oct. 19, 2021.
U.S. Appl. No. 18/249,577 filed Oct. 19, 2021.
U.S. Appl. No. 18/294,370 filed Feb. 1, 2024.
U.S. Appl. No. 18/294,403 filed Feb. 1, 2024.
U.S. Appl. No. 18/373,424 filed Sep. 27, 2023.
U.S. Appl. No. 18/376,274 filed Oct. 3, 2023.
U.S. Appl. No. 18/389,009 filed Nov. 13, 2023.
U.S. Appl. No. 18/415,080 filed Jan. 17, 2024.
U.S. Appl. No. 18/426,795 filed Jan. 30, 2024.
U.S. Appl. No. 18/549,387 filed Sep. 7, 2023.
U.S. Appl. No. 18/549,658 filed Sep. 8, 2023.
U.S. Appl. No. 18/553,625 filed Oct. 2, 2023.
U.S. Appl. No. 18/556,945 filed Oct. 24, 2023.
U.S. Appl. No. 18/558,502 filed Nov. 1, 2023.
U.S. Appl. No. 18/562,626 filed Nov. 20, 2023.
U.S. Appl. No. 18/563,672 filed Nov. 22, 2023.
U.S. Appl. No. 18/569,711 filed Dec. 13, 2023.
U.S. Appl. No. 18/569,778 filed Dec. 13, 2023.
U.S. Appl. No. 18/584,002 filed Feb. 22, 2024.
U.S. Appl. No. 18/610,523 filed Mar. 20, 2024.
U.S. Appl. No. 18/662,216 filed May 13, 2024.
U.S. Appl. No. 18/681,987 filed Feb. 7, 2024.
U.S. Appl. No. 18/682,006 filed Feb. 7, 2024.
U.S. Appl. No. 18/687,117 filed Feb. 27, 2024.
U.S. Appl. No. 18/688,023 filed Feb. 29, 2024.
U.S. Appl. No. 18/693,638 filed Mar. 20, 2024.
U.S. Appl. No. 18/694,090 filed Mar. 21, 2024.
U.S. Appl. No. 63/561,893 filed Dec. 11, 2023.
U.S. Appl. No. 63/596,012 filed Nov. 3, 2023.
U.S. Appl. No. 63/608,553 filed Dec. 11, 2023.
Wikipedia Article, "Decibel", https://web.archive.org/web/20200415219l7/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 17/645,821 mailed Jul. 2, 2024.
Final Office Action for U.S. Appl. No. 17/051,600 mailed Jun. 27, 2024.
Non-Final Office Action for U.S. Appl. No. 17/446,654 mailed Jun. 25, 2024.
Non-Final Office Action for U.S. Appl. No. 17/663,330 mailed Jul. 1, 2024.
U.S. Appl. No. 18/757,964 filed Jun. 28, 2024.
U.S. Appl. No. 18/758,025 filed Jun. 28, 2024.
"Oblong", Cambridge Dictionary, https://dictionary.cambridge.org/dictionary/english/oblong, 2024, 1 page.
Britannica , "Polyolefin", Britannica Online Encyclopedia, T. Editors of Encyclopaedia, https://www.britannica.com/science/polyolefin, Jul. 26, 2012.
Martin , et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Advisory Action for U.S. Appl. No. 17/446,256 mailed Nov. 19, 2024.
Advisory Action for U.S. Appl. No. 17/597,673 mailed Jan. 7, 2025.
Advisory Action for U.S. Appl. No. 17/653,137 mailed Nov. 20, 2024.
Advisory Action for U.S. Appl. No. 18/003,029 mailed Jan. 8, 2025.
Advisory Action for U.S. Appl. No. 18/164,800 mailed Jan. 8, 2025.
Corrected Notice of Allowability for U.S. Appl. No. 17/646,771 mailed Jan. 17, 2025.
Corrected Notice of Allowability for U.S. Appl. No. 18/426,795 mailed Dec. 4, 2024.
Final Office Action for U.S. Appl. No. 16/452,258 mailed Jan. 6, 2025.
Final Office Action for U.S. Appl. No. 17/446,654 mailed Dec. 18, 2024.
Final Office Action for U.S. Appl. No. 17/451,345 mailed Feb. 6, 2025.
Final Office Action for U.S. Appl. No. 17/595,747 mailed Dec. 12, 2024.
Final Office Action for U.S. Appl. No. 17/625,941 mailed Feb. 18, 2025.
Final Office Action for U.S. Appl. No. 17/653,314 mailed Jan. 30, 2025.
Final Office Action for U.S. Appl. No. 17/655,464 mailed Nov. 29, 2024.
Final Office Action for U.S. Appl. No. 17/664,487 mailed Jan. 13, 2025.
International Search Report and Written Opinion from International Application No. PCT/US2023/031432 mailed Feb. 29, 2024.
International Search Report and Written Opinion from International Application No. PCT/US2024/053681 mailed Jan. 27, 2025.
Issue Notification for U.S. Appl. No. 17/179,116 mailed Dec. 25, 2024.
Issue Notification for U.S. Appl. No. 17/447,123 mailed Nov. 13, 2024.
Issue Notification for U.S. Appl. No. 17/450,864 mailed Jan. 8, 2025.
Issue Notification for U.S. Appl. No. 17/529,769 mailed Feb. 19, 2025.
Issue Notification for U.S. Appl. No. 17/661,090 mailed Feb. 5, 2025.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/140,751 mailed Feb. 12, 2025.
Issue Notification for U.S. Appl. No. 18/198,464 mailed Nov. 20, 2024.
Issue Notification for U.S. Appl. No. 18/389,009 mailed Dec. 18, 2024.
Issue Notification for U.S. Appl. No. 18/426,795 mailed Feb. 19, 2025.
Non-Final Office Action for U.S. Appl. No. 17/446,256 mailed Dec. 13, 2024.
Non-Final Office Action for U.S. Appl. No. 17/653,137 mailed Jan. 28, 2025.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/907,125 mailed Dec. 13, 2024.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 17/051,585 mailed Dec. 26, 2024.

(56) References Cited

OTHER PUBLICATIONS

Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/596,629 mailed Jan. 29, 2025.
Notice of Allowance for U.S. Appl. No. 17/646,771 mailed Dec. 17, 2024.
Notice of Allowance for U.S. Appl. No. 17/663,330 mailed Nov. 20, 2024.
Notice of Allowance for U.S. Appl. No. 17/749,340 mailed Feb. 14, 2025.
Notice of Allowance for U.S. Appl. No. 18/134,857 mailed Feb. 20, 2025.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/754,736 mailed Nov. 20, 2024.
Restriction Requirement for U.S. Appl. No. 17/809,083 mailed Dec. 31, 2024.
U.S. Appl. No. 18/951,944 filed Nov. 19, 2024.
U.S. Appl. No. 18/957,011 filed Nov. 22, 2024.
U.S. Appl. No. 18/974,367 filed Dec. 9, 2024.
U.S. Appl. No. 18/982,930 filed Dec. 16, 2024.
U.S. Appl. No. 19/038,774 filed Jan. 28, 2025.
U.S. Appl. No. 19/039,165 filed Jan. 28, 2025.
U.S. Appl. No. 19/046,047 filed Feb. 5, 2025.
U.S. Appl. No. 19/047,728 filed Feb. 7, 2025.
U.S. Appl. No. 19/048,004 filed Feb. 7, 2025.
U.S. Appl. No. 19/049,501 filed Feb. 10, 2025.
U.S. Appl. No. 19/049,783 filed Feb. 10, 2025.
U.S. Appl. No. 19/058,726 filed Feb. 20, 2025.
U.S. Appl. No. 19/103,165 filed Feb. 11, 2025.
U.S. Appl. No. 63/181,709 filed Apr. 29, 2021.
U.S. Appl. No. 63/720,004 filed Nov. 13, 2024.
Non-Final Office Action for U.S. Appl. No. 17/179,116 mailed Feb. 26, 2024.
Non-Final Office Action for U.S. Appl. No. 18/003,029 mailed Mar. 26, 2024.
Final Office Action for U.S. Appl. No. 16/904,868 mailed Mar. 10, 2022.
International Search Report and Written Opinion from International Application No. PCT/US2022015471 mailed May 16, 2022.
Non-Final Office Action for U.S. Appl. No. 16/433,773 mailed Apr. 21, 2022.
Non-Final Office Action for U.S. Appl. No. 16/905,400 mailed Apr. 27, 2022.
Notice of Allowance for U.S. Appl. No. 16/899,956 mailed Apr. 19, 2022.
Notice of Allowance for U.S. Appl. No. 17/330,657 mailed Mar. 16, 2022.
U.S. Appl. No. 17/654,156 filed Mar. 9, 2022.
U.S. Appl. No. 17/655,464 filed Mar. 18, 2022.
U.S. Appl. No. 63/094,646 filed Oct. 21, 2020.
Advisory Action for U.S. Appl. No. 17/051,585 mailed Oct. 8, 2024.
Advisory Action for U.S. Appl. No. 17/444,792 mailed Jul. 8, 2024.
Advisory Action for U.S. Appl. No. 17/451,345 mailed Jul. 3, 2024.
Advisory Action for U.S. Appl. No. 18/134,857 mailed Oct. 23, 2024.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/664,914 mailed Aug. 9, 2024.
Final Office Action for U.S. Appl. No. 16/433,773 mailed Sep. 9, 2024.
Final Office Action for U.S. Appl. No. 17/051,585 mailed Jul. 5, 2024.
Final Office Action for U.S. Appl. No. 17/446,256 mailed Aug. 7, 2024.
Final Office Action for U.S. Appl. No. 17/451,354 mailed Oct. 28, 2024.
Final Office Action for U.S. Appl. No. 17/597,673 mailed Oct. 22, 2024.
Final Office Action for U.S. Appl. No. 17/653,137 mailed Aug. 7, 2024.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/164,800 mailed Oct. 22, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
Issue Notification for U.S. Appl. No. 16/369,676 mailed Oct. 2, 2024.
Issue Notification for U.S. Appl. No. 16/452,145 mailed Oct. 23, 2024.
Issue Notification for U.S. Appl. No. 17/326,980 mailed Jul. 10, 2024.
Issue Notification for U.S. Appl. No. 17/448,811 mailed Jul. 3, 2024.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/662,700 mailed Oct. 23, 2024.
Issue Notification for U.S. Appl. No. 17/664,914 mailed Nov. 6, 2024.
Non-Final Office Action for U.S. Appl. No. 16/478,180 mailed Aug. 7, 2024.
Non-Final Office Action for U.S. Appl. No. 17/378,015 mailed Jul. 5, 2024.
Non-Final Office Action for U.S. Appl. No. 17/444,792 mailed Oct. 30, 2024.
Non-Final Office Action for U.S. Appl. No. 17/451,345 mailed Jul. 25, 2024.
Non-Final Office Action for U.S. Appl. No. 17/597,408 mailed Aug. 15, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/653,314 mailed Aug. 29, 2024.
Non-Final Office Action for U.S. Appl. No. 17/749,340 mailed Aug. 14, 2024.
Non-Final Office Action for U.S. Appl. No. 17/757,311 mailed Oct. 22, 2024.
Non-Final Office Action for U.S. Appl. No. 17/758,316 mailed Aug. 28, 2024.

(56) References Cited

OTHER PUBLICATIONS

Non-Final Office Action for U.S. Appl. No. 18/139,523 mailed Aug. 26, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/452,145 mailed Jul. 11, 2024.
Notice of Allowance for U.S. Appl. No. 16/904,868 mailed Sep. 29, 2024.
Notice of Allowance for U.S. Appl. No. 17/179,116 mailed Sep. 13, 2024.
Notice of Allowance for U.S. Appl. No. 17/447,123 mailed Jul. 26, 2024.
Notice of Allowance for U.S. Appl. No. 17/450,864 mailed Sep. 18, 2024.
Notice of Allowance for U.S. Appl. No. 17/501,591 mailed Jul. 31, 2024.
Notice of Allowance for U.S. Appl. No. 17/661,090 mailed Oct. 30, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Jul. 30, 2024.
Notice of Allowance for U.S. Appl. No. 18/389,009 mailed Aug. 28, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/878,268 mailed Sep. 20, 2024.
U.S. Appl. No. 15/611,587 filed Jun. 1, 2017.
U.S. Appl. No. 17/013,822 filed Sep. 7, 2020.
U.S. Appl. No. 18/728,604 filed Jul. 12, 2024.
U.S. Appl. No. 18/828,559 filed Sep. 9, 2024.
U.S. Appl. No. 18/834,115 filed Jul. 29, 2024.
U.S. Appl. No. 18/834,176 filed Jul. 29, 2024.
U.S. Appl. No. 18/834,340 filed Jul. 30, 2024.
U.S. Appl. No. 18/835,068 filed Aug. 1, 2024.
U.S. Appl. No. 18/835,444 filed Aug. 2, 2024.
U.S. Appl. No. 18/836,204 filed Aug. 6, 2024.
U.S. Appl. No. 18/841,630 filed Aug. 26, 2024.
U.S. Appl. No. 18/851,197 filed Sep. 26, 2024.
U.S. Appl. No. 18/886,306 filed Sep. 16, 2024.
U.S. Appl. No. 18/903,592 filed Oct. 1, 2024.
U.S. Appl. No. 18/925,921 filed Oct. 24, 2024.
U.S. Appl. No. 18/930,014 filed Oct. 29, 2024.
U.S. Appl. No. 18/931,853 filed Oct. 30, 2024.
U.S. Appl. No. 63,564,696 filed Mar. 13, 2024.
U.S. Appl. No. 63/568,615 filed Mar. 22, 2024.
U.S. Appl. No. 63/683,428 filed Aug. 15, 2024.
U.S. Appl. No. 63/711,438 filed Oct. 24, 2024.
U.S. Appl. No. 63/711,445 filed Oct. 24, 2024.
"Dictionary.com, Abut Definition and Meaning", Dictionary.com, https://www.dictionary.com/browse/abut, 2024, 1 page.

* cited by examiner

ACOUSTIC SILENCER FOR A URINE SUCTION SYSTEM

CROSS-REFERENCE TO RELATED APPLICATION(S)

This application claims priority to U.S. Provisional Patent No. 63/159,210 filed on Mar. 10, 2021, the disclosure of which is incorporated herein, in its entirety, by this reference.

BACKGROUND

In various circumstances, a person may have limited or impaired mobility such that typical urination processes are challenging or impossible. For example, a person may experience or have a disability that impairs mobility. A person may have restricted travel conditions such as those experienced by pilots, drivers, and workers in hazardous areas. Additionally, sometimes urine collection is needed for monitoring purposes or clinical testing.

In these and other circumstances, a urine collection device can be utilized to collect and retain evacuated urine. After the urine has been evacuated, the urine may need to be removed from the urine collection device. For example, a urine suction device can be used to remove urine evacuated into the urine collection device.

Devices, systems, and methods which more efficiently, hygienically, and discreetly remove or otherwise transport urine can be desirable.

SUMMARY

Embodiments are directed to a urine suction device including a motor, a pump, a conduit, and an acoustic silencer. The pump is configured to be driven by the motor. The pump is configured to extract urine from a urine collection device. The conduit is coupled to the pump and configured to exhaust a fluid from the pump. The acoustic silencer is in fluid communication with the conduit and the pump. The acoustic silencer defines a non-linear airflow path between an inlet and an outlet of the acoustic silencer.

In another embodiment of the present disclosure, a system for transporting urine away from a user is disclosed. The system can include a urine collection device, a container, and a suction device coupled to the urine collection device. The suction device is configured to draw urine from the urine collection device into the container. The urine suction device can include a motor, a pump, a conduit, and an acoustic silencer. The pump is configured to be driven by the motor and extract urine from the urine collection device. The conduit is coupled to the pump and configured to exhaust a fluid from the pump. The acoustic silencer is in fluid communication with the conduit and the pump. The acoustic silencer defines a non-linear airflow path between an inlet and an outlet of the acoustic silencer.

Embodiments are directed to a method for reducing noise pollution of a urine suction device with an acoustic silencer. While power is being supplied (e.g., electrical power, pneumatic power, etc.), the motor can actuate a pump of the urine suction device to transport urine away from the user. The method also includes routing one or more acoustic waves generated by the pump to the acoustic silencer through a conduit. The method also includes providing the one or more acoustic waves at an inlet of the acoustic silencer. The method can also include attenuating at least a portion of the one or more acoustic waves along an airflow path formed within the acoustic silencer. The method can also include releasing the one or more acoustic waves from an outlet of the acoustic silencer.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1:
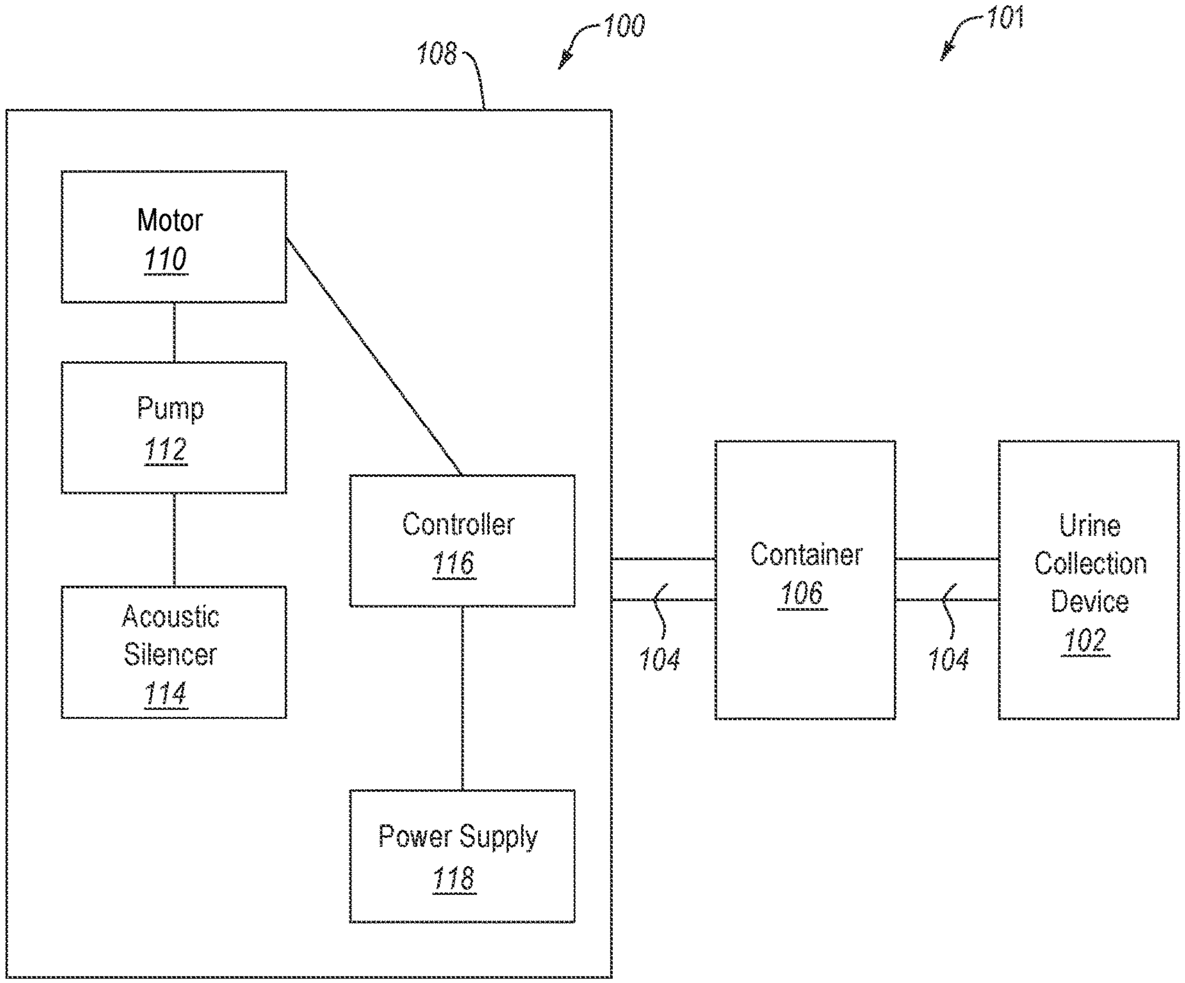
FIG. 1 is a block diagram of a urine suction device coupled to a urine collection device, according to an embodiment.

Embodiments described herein are directed to urine suction devices suitable for discreetly pumping urine from a urine collection device and away from the body of a person. The embodiments of the urine suction devices described herein may be fluidly coupled or otherwise attached to a urine collection device positioned in a pubic region of a user to collect urine or other fluids expelled by the user. While this disclosure primarily describes the suction device as a urine suction device, it will be appreciated that the embodiments disclosed herein can also be utilized to collect other fluids discharged from a user.

In embodiments, the urine suction device includes a housing forming or defining an interior volume. One or more components of the urine suction device can be at least partially disposed within the interior volume. For example, a motor (e.g., an electric or pneumatic motor) and a pump can be disposed within the housing and operate to provide a suction force. In some embodiments, the housing can be omitted. While the urine suction device is operating (e.g., pumping urine from a urine collection device), the pump and/or another component of the urine suction device can generate an audible noise (e.g., one or more acoustic waves). In some embodiments, the pump can include a conduit which enables air to exhaust from the pump. As pumped air is exhausted from the conduit, acoustic waves can emit from the conduit to generate audible noise. This noise can be embarrassing and unflattering to the user of the urine suction device, especially while the user in a public space or has company. As such, reducing or eliminating acoustic waves generated by the urine suction device can be desirable to provide a urine suction device that is more discreet and less obtrusive.

In some embodiments, the urine suction device can include a motor and a pump that is driven by the motor. For example, the motor can be coupled to a diaphragm within the pump which draws air into and out of the pump. While driven by the motor, the pump can generate a negative pressure that can draw urine from a urine collection device. The urine suction device can include a conduit coupled to the pump which enables fluids (e.g., air) to be exhausted from the pump. The urine suction device includes an acoustic silencer in fluid communication with the conduit and pump. For example, the acoustic silencer can include an inlet which is attached or otherwise affixed to the conduit.

The acoustic silencer can define one or more non-linear airflow path between the inlet and an outlet of the acoustic silencer to attenuate or otherwise reduce one or more acoustic waves generated by the pump and propagated through the conduit. Components and/or structures disposed within the acoustic silencer can define a plurality of non-linear airflow paths within the acoustic silencer. In other words, acoustic waves that propagate into the acoustic silencer can be directed and guided along one or more paths within the acoustic silencer which cause the acoustic waves to be attenuated or otherwise reduce the magnitude of the acoustic waves. While the non-linear airflow path is described as a singular path in some embodiments, the non-linear airflow path can include multiple paths that diverge and/or intersect relative to components and/or structures within the acoustic silencer.

In some embodiments, the acoustic silencer can include an enclosure and one or more components which attenuate acoustic waves within the enclosure. For example, the acoustic silencer can include noise dampening materials, such as, foam, mineral wool, polyester, and/or any other material known to dampen or attenuate acoustic waves. Additionally, or alternatively, the acoustic silencer can include one or more components which attenuate acoustic waves within the enclosure by redirecting the acoustic waves to generate destructive interference. In other words, one or more components or structures within the acoustic silencer can direct the acoustic waves along the non-linear airflow path which attenuates the acoustic waves as they propagate within the acoustic silencer. For example, the acoustic silencer can include multiple internal chambers, one or more conduits, one or more baffles, internal walls, plates, a combination thereof, or any other element capable of directing acoustic waves along the non-linear airflow path.

Figure 2A:
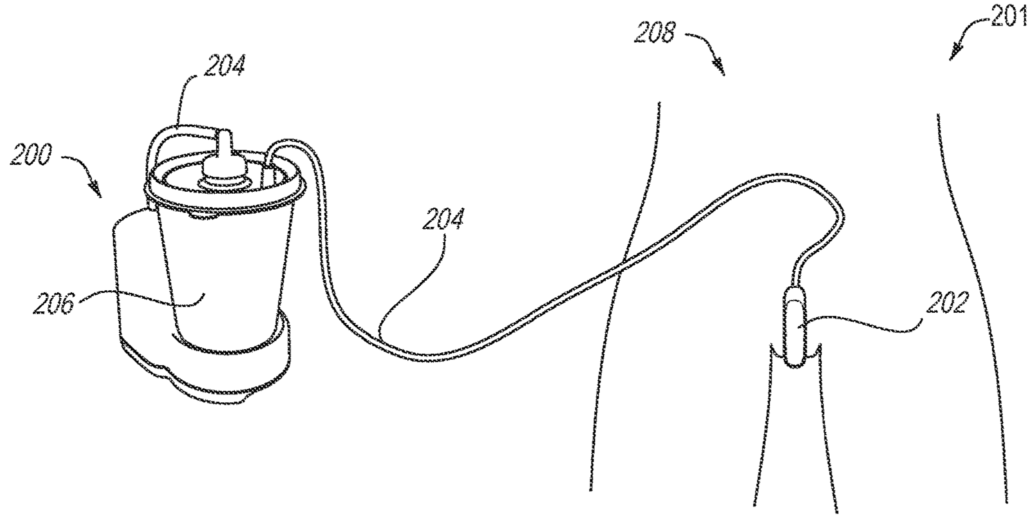
FIG. 2A is an isometric view of a urine suction device and a urine collection device operably associated with a user, according to an embodiment.

FIG. 1 shows a block diagram of a urine collection system 101 including a urine suction device 100 coupled to a urine collection device 102, according to an embodiment. The urine suction device 100 can be coupled to the urine collection device 102 using one or more tubes 104 and a container 106. For example, a suction force generated by the urine suction device 100 can draw urine or other fluids from the urine collection device 102, through the tube 104, and into the container 106. While this embodiment illustrates the urine suction device 100 and the container 106 as separate and distinct, the container 106 can be incorporated into or retained by the urine suction device 100 in other embodiments (as shown in FIGS. 2A-3).

The urine suction device 100 can include a housing 108, a motor 110, a pump 112, an acoustic silencer 114, a controller 116, and a power supply 118. The housing 108 can define an internal volume and one or more of the components of the urine suction device 100 (e.g., the motor 110, the pump 112, the acoustic silencer 114, the controller 116, the power supply 118, etc.) can be disposed within the internal volume. For example, one or more recesses or attachment features (not shown) can be molded machined or affixed to the housing 108 to provide an attachment surface for one or more of the components of the urine suction device 100. As shown in FIGS. 2A-3, the housing 108 can also form a recess or cavity for retaining the container 106. The recess or cavity can engage a base portion of the container 106 to retain the container 106 to the urine suction device 100. The housing 108 can be assembled using one or more distinct pieces that are adhered, affixed, or otherwise assembled to form the housing 108. For example, the housing 108 can be formed of one or more molded, co-molded, machined, or stamped elements. The housing 108 can be manufactured from a polymer, ceramic, metal, a combination thereof, or any other material that can provide the functionality described herein.

While not depicted in FIG. 1, the housing 108 can support one or more input devices, such as, buttons, toggles, switches, dials, touchscreens, levers, any combination thereof, or any other input device. The one or more input devices can cause the urine collection device 100 to alter its operational state, for example, by causing the controller 116 to supply electrical power to the motor 110 to generate suction via the pump 112. The housing 108 can include various through-holes, ports, or apertures which accommodate the one or more input components. Additionally, or alternatively, the housing 108 can include various through-holes or apertures which accommodate tubes, wires, or any other fluid or electrical conduit that may need to extend into the internal volume of the housing 108. For example, an electrical cable can extend from an electrical wall outlet and through an aperture within the housing 108 to the power supply 118 to electrically power the urine suction device 100. The housing 108 will be further described below with reference to FIGS. 2A-3.

In embodiments, the motor 110 can be any electrical motor or pneumatic motor capable of operating the pump 112 (i.e., causing the pump 112 to generate a negative pressure within the container 106 and/or the urine collection device 102). For example, the motor 110 can operate on alternating current (AC) or direct current (DC) and can be a brushless motor or a brushed motor. Additionally, or alternatively, the motor 110 can be DC series motor, a DC shunt motor, a stepper motor, a linear motor, a servo motor, a combination thereof, or any other motor capable of the functionality described herein. The motor 110 can drive the pump 112 to generate a suction force to draw urine out of the urine collection device 102, through the tube 104, and into the container 106. During operation (e.g., when electrical or pneumatic power is being supplied to the motor), the motor 110 can generate noise, such as, acoustic waves resultant of movement and vibration associated with operation. At least a portion of these acoustic waves generated by vibration of the motor 110 can be transferred to the pump 112. The acoustic silencer 114 can also at least partially attenuate any acoustic waves generated by the motor 110 that are transferred to the pump 112 and propagate through the conduit. The motor 110 will be further described below with reference to FIGS. 2A-3.

The pump 112 can be any pump capable of generating a suction force which can draw urine from the urine collection device 102. For example, the pump 112 can be a rotary lobe or gear pump, a diaphragm pump, a piston, a screw pump, a combination thereof, or any other pump capable of the functionality described herein. In some embodiments, the pump 112 can include a diaphragm (not shown) that draws air into the pump on a first stroke and exhausts air out of the diaphragm on a second stroke. The first and second strokes of the diaphragm can be actuated by rotation of the motor 110. During operation (e.g., when rotation of the motor causes actuation of the pump), the pump 112 can generate noise, such as, acoustic waves resultant of movement and vibration associated with operation. At least some of these acoustic waves can propagate along a conduit coupled to the pump 112. The conduit can exhaust air drawn into the pump 112, for example, on the second stroke of the diaphragm. The pump 112 will be further described below with reference to FIGS. 2A-3D.

In some embodiments, the acoustic silencer 114 can be in fluid communication with the conduit and the pump 112. For example, the conduit can be coupled to the pump 112 and the acoustic silencer 114 such that air exhausted from the pump 112 propagates through the conduit and into the acoustic silencer 114. The conduit can be coupled, adhered, fastened, molded, welded, or otherwise affixed to the pump 112 by any mechanism. The conduit can be coupled, adhered, fastened, molded, welded, or otherwise affixed to the acoustic silencer 114 by any mechanism.

In some embodiments, the acoustic silencer 114 can include noise dampening materials and/or one or more components which attenuate acoustic waves within the acoustic silencer 114 by redirecting the acoustic waves to generate destructive interference. The one or more components within the acoustic silencer 114 can direct the acoustic waves along the non-linear airflow path which attenuates the acoustic waves as they propagate within the acoustic silencer 114. For example, the acoustic silencer can include multiple internal chambers, one or more conduits, one or more baffles, internal walls, plates, a combination thereof, or any other structure capable of directing acoustic waves along the non-linear airflow path. In some embodiments, the acoustic silencer 114 can attenuate or otherwise reduce an amplitude of the acoustic waves by at least 5%, about 5% to about 15%, about 15% to about 30%, about 30% to about 50%, about 50% to about 75%, or more than 75%. The acoustic silencer 114 will be further described below with reference to FIGS. 2A-3.

In some embodiments, one or more of the components of the urine suction device 100 can be operably coupled to the controller 116. For example, the controller 116 can be disposed within the internal volume of the housing 108 and include one or more processors and memory storage having one or more operational programs stored therein. When executed by the processor, the one or more operational programs can cause the urine suction device 100 to operate (e.g., draw urine or other fluid from a urine collection device). The controller 116 can be communicatively coupled to one or more of the components of the urine suction device 100 (e.g., the motor 110, the pump 112, the power supply 118, etc.). The controller 116 will be further described below with reference to FIGS. 2A-3.

The power supply 118 may be operably coupled to the controller 116, the motor 110, the pump 112, or any other components of the urine suction device 100 to provide electrical power to the urine suction device 100. For example, the power supply 118 may include one or more batteries (e.g. lithium-ion, nickel-cadmium, nickel-metal hydride, etc.) or portable chargers (e.g., power banks). The one or more batteries may be rechargeable. In examples, the one or more batteries may be modular battery packs, which may be removed and replaced. In examples, the one or more batteries have a connection for charging, such as a connection for the portable charger. The power supply 118 may be a replaceable and rechargeable battery, such as a 12 volt battery. The rechargeable battery may be a lithium ion battery, lithium-ion polymer, a nickel-cadmium battery, nickel-metal hydride, lead acid, etc., batteries. The power supply 118 may include a plurality of rechargeable batteries. The rechargeable battery may be at least a 1 volt battery, such as 1.5 volts to 3 volts, 3 volts to 6 volts, 6 volts to 9 volts, 9 volts to 12 volts, 12 volts to 15 volts, 15 volts to 24 volts, greater than 12 volts, less than 24 volts, or less than 15 volts.

In examples, the power supply 118 may include a cord or wired connection for connecting to a power outlet. For example, the power supply 118 may include 110 volt, 220 volt, or similar connections. The cord may allow the user to plug the urine suction device 100 into a power outlet in a room, an extension cord, or a power station or power bank (e.g., battery pack or bank). Accordingly, the power supply 118 may include a wall outlet, the extension cord, or a power station or power bank. In examples, the power supply 118 may include both a wired connection for coupling to a power source and a battery pack. Accordingly, the urine suction device 100 may be run with our without battery power. In examples, the wired connection may be provided as a detachable power cord which may be removed from the urine suction device 100. The wired connection may serve to recharge the battery pack and provide power to the urine suction device 100.

The container 106 can be distinct from the urine suction device 100 or releasably retained on the housing 108 of the urine collection device 100 (as shown in FIGS. 2A-3). The container 106 can be any container capable of storing urine or other fluids that are extracted from the urine collection device 102 by a suction force applied by the urine suction device 100. As such, the container 106 can be manufactured of any rigid or flexible material capable of reliably retaining fluid. The container 106 can be machined, molded, co-molded, or otherwise manufactured from any material, such as, a polymer, a metal, a ceramic, or a combination thereof. The container 106 will be further described below with reference to FIGS. 2A-3.

The urine collection device 104 can be any urine collection device presently available or otherwise developed in the future. The urine collection device 104 may be adapted to extract urine or other fluids discharged by female and/or male persons. One suitable non-limiting example of a urine collection device that can be used is an external catheter, available from PureWick, Inc. Any urine collection device capable of collecting discharged urine from a male or female user can be utilized with the present disclosure. For example, the urine collection devices described in U.S. Patent Publication No. 2019/0282391 filed 6 Jun. 2019 and U.S. Pat. No. 10,390,989 filed 8 Sep. 2016, the disclosures of which are incorporated herein, in their entirety, by this reference.

Figure 2B:
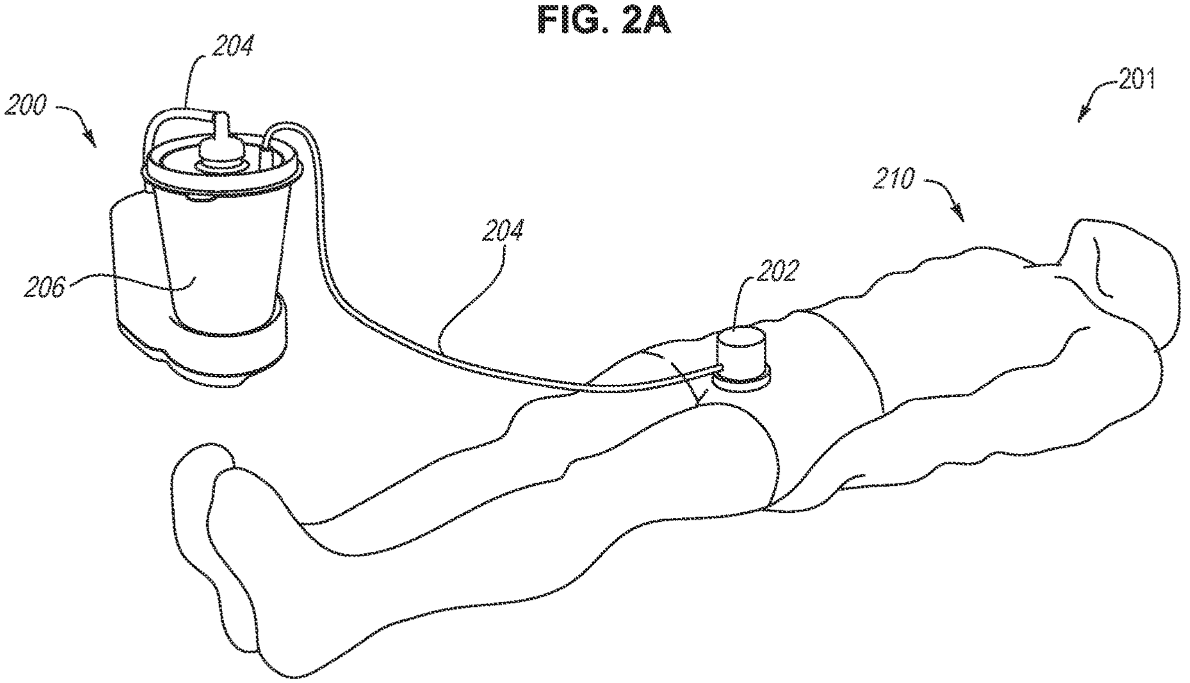
FIG. 2B is an isometric view of a urine suction device and a urine collection device operably associated with a user, according to an embodiment.
Figure 3:
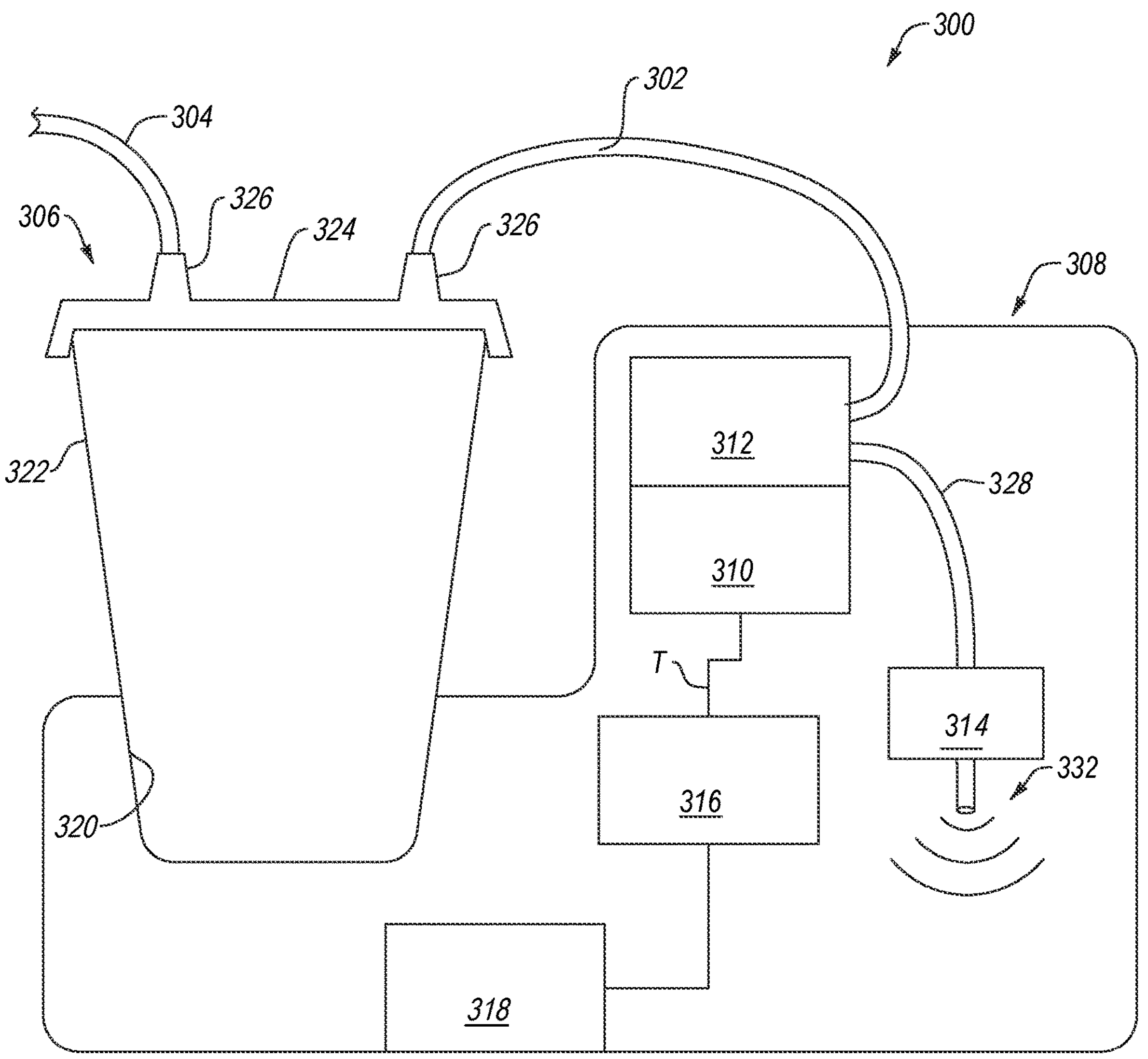
FIG. 3 is a schematic cross-section view of a urine suction device, according to an embodiment.

FIGS. 2A and 2B show isometric views of a urine collection system 201 including a urine suction device 200 and a urine collection device 202, according to an embodiment. Except as otherwise disclosed herein system 201 (e.g., the urine suction device 200 and the urine collection device 202) may be the same or substantially similar to any of the urine collection systems disclosed herein. The urine collection system 201 includes a first tube 204 extending from the urine suction device 200 to a container 206 and a second tube 204 extending from the container 206 to the urine collection device 202. The urine collection device 202 can be disposed on a female user 208 (as shown in FIG. 2A) or a male user 210 (as shown in FIG. 2B). On female users, the urine collection device 202 can be placed between the legs or labia and held snugly against the external urethra by the pressure of friction from the user's body, by the pressure of the legs or by such means as an undergarment, elastic strips, and/or adhesive tape. Examples of the urine collection device 202 configured to be used with female users are disclosed in U.S. Pat. No. 10,973,678 filed on Jun. 2, 2017, U.S. Pat. No. 10,390,989 filed on Sep. 8, 2016, U.S. Pat. No. 10,226,376 filed on Jun. 3, 2017, PCT Patent Application No. PCT/2022/011281 filed on Jan. 5, 2022, and PCT Patent Application No. PCT/US2020/042262 filed on Jul. 16, 2020, the disclosures of each of which is incorporated herein, in its entirety, by this reference. In male applications, the urine collection device 202 can be positioned around the penis. Examples of the urine collection 202 configured to be used with male users are disclosed in PCT Patent Application No. PCT/US2021/039866 filed on Jun. 30, 2021, U.S. patent application Ser. No. 16/433,773 filed on Jun. 6, 2019, PCT Patent Application No. PCT/2022/011281 filed on Jan. 5, 2022, and PCT Patent Application No. PCT/US2020/042262 filed on Jul. 16, 2020, the disclosures of each of which is incorporated herein, in its entirety, by this reference. The urine suction device 200 can generate a negative pressure within the container 206 to draw or extract urine or other fluids from the urine collection device 202 into the container 206.

FIG. 3 show a non-limiting example of a urine suction device 300, according to an embodiment. FIG. 3 shows a schematic cross-section view of the urine suction device 300, according to some embodiments. The urine suction device 300 can be substantially similar to and can include some or all of the features of the urine suction devices 100 and 200. For example, one or more tubes 304 can place the urine suction device 300 in fluid communication with a container 306 and/or a urine collection device (not shown).

The urine suction device 300 can include a housing 308, a motor 310, a pump 312, an acoustic silencer 314, a controller 316, and a power supply 318. The motor 310 can be substantially similar to and can include some or all of the features of the motor 110 described with reference to FIG. 1. For example, the motor 310 can drive the pump 312 to generate a suction force to draw urine out of the urine collection device (not shown), through the tube 304, and into the container 306. The pump 312 can be substantially similar to and can include some or all of the features of the pump 112 described with reference to FIG. 1. For example, the pump 312 can be a rotary lobe or gear pump, a diaphragm pump, a piston, a screw pump, a combination thereof, or any other pump capable of the functionality described herein. The pump 312 can apply a suction force to the container 306 through a tube 302. The pump 312 and the container 306 can be in fluid communication through the tube 302. The controller 316 can be substantially similar to and can include some or all of the features of the controller 116 described with reference to FIG. 1. For example, the controller 316 can be communicatively coupled to one or more of the components of the urine suction device 300 (e.g., the motor 310, the pump 312, the power supply 318, etc.) through electrical traces T. The power supply 318 can be substantially similar to and can include some or all of the features of the power supply 118 described with reference to FIG. 1. For example, the power supply 318 may be operably coupled to the controller 316, the motor 310, the pump 312, or any other components of the urine suction device 300 to provide electrical power to the urine suction device 300.

The housing 308 can be substantially similar to and can include some or all of the features of the housing 108 described with reference to FIG. 1. While the housing 308 is illustrated as having a particular cross-sectional shape, the cross-sectional shape illustrated in FIG. 3 merely represents one example cross-sectional shape of many. Similarly, while the components of the urine suction device 300 (e.g., the motor 310, the pump 312, the acoustic silencer 314, the controller 316, and the power supply 318, etc.) are illustrated in respective positions within the housing 308, one or more of the components can be positioned elsewhere within the housing 308 or external to the housing 308. The housing 308 can form a cavity or recess 320 for retaining the container 306. The cavity or recess 320 can have a profile which substantially matches a base portion of the container 306 such that base portion of the container 306 is reliably retained within the recess 320.

The container 306 can include a body 322 and a lid 324. The body 322 can retain or store a quantity of fluid, such as, urine or other fluid which is extracted or pumped from a urine collection device (not shown). The lid 324 can be affixed to the body 322, for example, by a threaded engagement, a friction fit engagement, a protrusion interlocking engagement, or any other mechanism capable of retaining the lid 324 to the body 322. The lid 324 can include one or more inlets 326 which receive the respective tubes 302, 304 or other fluid conduits and place the container 306 in fluid communication with a urine collection device (not shown) and/or the urine suction device 300. The one or more inlets 326 can form respective apertures within the lid 324 to place the container 306 in fluid communication with a urine collection device (not shown) and/or the urine suction device 300. While the one or more inlets 326 are illustrated as being formed on the lid 324, the one or more inlets 326 can additionally, or alternatively, be formed on the body 322 of the container 306.

In some embodiments, the pump 312 can intake fluid (e.g., air) through the tube 302 and exhaust the fluid through a conduit 328. In other words, while the pump 312 is being driven by the motor 310, fluid (e.g., air) can be drawn or sucked into the pump 312 and exhausted through the conduit 328. This process can generate audible acoustic waves which alert persons that urine or other fluid is currently being drawn or extracted from the urine collection device. For example, operation of the pump 312 (e.g., oscillating a diaphragm within the pump 312) and exhausting fluid through the conduit 328 can generate acoustic waves which are detectable by persons located near the urine suction device 300.

The acoustic silencer 314 can be in fluid communication with the conduit 328 and the pump 312. For example, the conduit 328 can be coupled to the pump 312 and the acoustic silencer 314 such that air exhausted from the pump 312 propagates through the conduit and into the acoustic silencer 314. The air exhausted through the conduit 328 can form acoustic waves which have properties (e.g., wavelength, frequency, amplitude, etc.) correlating to operation of the pump 312 and the motor 310.

In some embodiments, the acoustic silencer 314 can include noise dampening materials and/or one or more components which attenuate acoustic waves within the acoustic silencer 314 by redirecting the acoustic waves to generate destructive interference or otherwise muffle the acoustic waves. The one or more components within the acoustic silencer 314 can direct the acoustic waves along the non-linear airflow path which attenuates the acoustic waves as they propagate within the acoustic silencer 314. For example, the acoustic silencer can include multiple internal chambers, one or more conduits, one or more baffles, internal walls, plates, a combination thereof, or any other structure capable of directing acoustic waves along the non-linear airflow path.

In some embodiments, the acoustic silencer 314 can attenuate or otherwise reduce an amplitude of the acoustic waves by at least 5%, about 5% to about 15%, about 15% to about 30%, about 30% to about 50%, about 50% to about 75%, or more than 75%. The acoustic silencer can attenuate or otherwise reduce one or more acoustic waves having frequencies within a range of about 20 Hz to about 4 kHz. In some embodiments, the one or more acoustic waves can be attenuated or reduced by at least about 1 dB, at least about 5 dB, at least about 10 dB, at least about 15 dB, at least about 20 dB, at least about 25 dB, at least about 30 dB, at least about 35 dB, at least about 40 dB, at least about 45 dB, at least about 50 dB, about 1 dB to about 5 dB, about 2.5 dB to about 7.5 dB, about 5 dB to about 15 dB, about 10 dB to about 20 dB, about 15 dB to about 25 dB, about 20 dB to about 30 dB, about 25 to about 35 dB, about 30 dB to about 40 dB, about 35 dB to about 45 dB, about 40 dB to about 50 dB. The acoustic silencer 114 will be further described below with reference to FIGS. 4-6.

Figure 4:
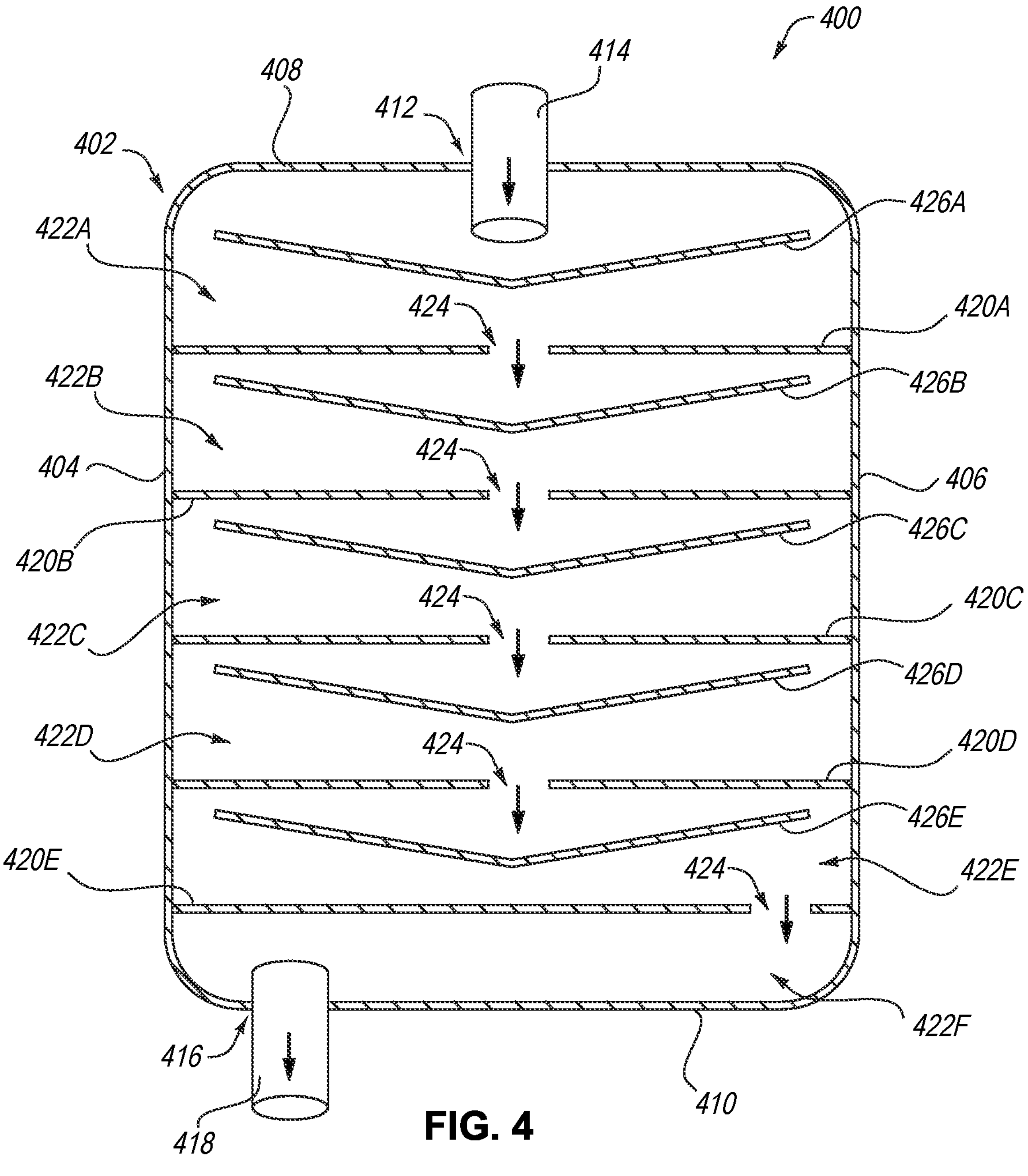
FIG. 4 is a schematic cross-section view of an acoustic silencer for a urine suction device, according to an embodiment.

FIG. 4 shows a schematic cross-section view of an acoustic silencer 400 for a urine suction device, according to an example embodiment. The acoustic silencer 400 may be used in any of the urine suction devices disclosed herein and, except as otherwise disclosed herein, may be the same as any of the silencers disclosed herein. The acoustic silencer 400 includes an enclosure 402 having a three-dimensional shape, such as, a cube, a cylinder, a cone, a sphere, an ellipsoid, another three-dimensional geometric shape, or a combination thereof. For example, the enclosure 402 can include a first sidewall 404 and a second sidewall 406. In some embodiments, the first and second sidewalls 404, 406 can form a singular sidewall that wraps around a periphery of the enclosure 402, such as, when the enclosure 402 forms a circular or elliptic cylinder. In some embodiments, the first and second sidewalls 404, 406 can distinct and separate, such as, when the enclosure 402 forms a cube or rectangular cuboid.

In some embodiments, the enclosure 402 can include a third sidewall 408 and a fourth sidewall 410. The third sidewall 408 can include an inlet 412 placing the acoustic silencer 400 in fluid communication with a conduit 414 (e.g., conduit 328). For example, the conduit 414 can be extended through the inlet 412. In some embodiments, the inlet 412 can form a projection which is received within or surrounds a portion of the conduit 414 to place the conduit 414 in fluid communication with the acoustic silencer 400. While the inlet 412 is illustrated as a through-hole or aperture in FIG. 4, the inlet 412 can be any structure or element enabling fluid communication between the acoustic silencer 400 and the conduit 414.

The fourth sidewall 410 can include an outlet 416 placing the acoustic silencer 400 in fluid communication with an external environment (e.g., an internal volume of the housing 308, an environment external to the housing 308, etc.). For example, the outlet 416 can include a conduit 418 that releases any residual acoustic waves from the acoustic silencer 400. While the outlet 416 is illustrated as a conduit 418 in FIG. 4, the outlet 416 can be any structure or element enabling fluid communication between the acoustic silencer 400 and an environment external to the acoustic silencer 400. The enclosure 402 can be manufactured out of any material including, polymers, ceramics, metals, or combinations thereof. The enclosure 402 can be formed using any manufacturing process, such as, molding, machining, stamping, hydroforming, or a combination thereof.

Acoustic waves within the acoustic silencer 400 can propagate or travel along a non-linear airflow path that extends between the conduit 414 and conduit 418 of the acoustic silencer 400. In some embodiments, the non-linear airflow path, as illustrated as directional arrows throughout the acoustic silencer 400, can be a singular path along which acoustic waves are directed to travel within the acoustic silencer 400. For example, the acoustic waves can enter the acoustic silencer through a single inlet (e.g., inlet 412) and exit the acoustic silencer 400 through a single outlet (e.g., outlet 416). However, in some examples, the acoustic waves can enter through more than one inlet and exit through one or more outlets. Additionally, or alternatively, components and/or structures disposed within the acoustic silencer 400 can define a plurality of non-linear airflow paths within the acoustic silencer 400. In other words, while the non-linear airflow path is described as a singular path in some embodiments, the non-linear airflow path can include multiple paths that diverge and/or intersect.

In embodiments, the acoustic silencer 400 can include one or more dividers 420A-E which at least partially separate an internal cavity of the enclosure 402 into chambers 422A-F. Each of the one or more chambers 422A-F can function as an echo chamber wherein the acoustic waves reverberate and destructively interfere to reduce or diminish the amplitude of the acoustic waves. While each of the dividers 420A-E are illustrated as planar or flat, one or more of the dividers 420A-E can be curved or include a bend in some embodiments. Each of the one or more dividers 420A-E can form at least one aperture 424 (e.g., one aperture 424) providing fluid communication between the chambers 422A-F. Each aperture 424 can be formed along the divider 420. For example, the aperture 424 can be disposed on the divider 420E and adjacent the second sidewall 406 of the enclosure 402 while the aperture 424 can be disposed at a mid-section of the divider 420A. Each of the one or more dividers 420A-E can be manufactured out of any material including, polymers, ceramics, metals, or combinations thereof. For example, each of the one or more dividers 420A-E can be metal or plastic sheets which are welded (e.g., sonic welded) or otherwise affixed between the first and second walls 404, 406. Each of the one or more dividers 420A-E can be formed using any manufacturing process, such as, molding, machining, stamping, hydroforming, or a combination thereof.

In embodiments, the acoustic silencer 400 can include one or more baffles or structures 426A-E (e.g., one, at least one, two or more, three or more, etc.) that direct or guide acoustic waves along the non-linear airflow path. Each of the one or more baffles 426A-E can include planar surfaces, curved surfaces, angled surfaces, perforated surfaces, slotted surfaces, or combinations thereof. For example, each of the baffles 426A-E can be shaped or formed to resemble a "V" or planar portions angled relative to one another such that one or more acoustic waves propagating along the non-linear airflow path (e.g., through an aperture 424) are reverberated or reflected to cause destructive interference.

In embodiments, one or more acoustic waves can propagate out of the inlet 412 and reflect off of the baffle 426A.

The one or more acoustic waves can continue to repeatedly reflect between the baffle 426A and the third sidewall 408 until the one or more acoustic waves propagate through gap regions 428 between the baffle 426A and the enclosure 402. Subsequently, at least a portion of the one or more acoustic waves can repeatedly reflect between the baffle 426A and the divider 420A until the one or more acoustic waves propagate through the aperture 424 formed in the divider 420A. This process can continue as the one or more acoustic waves propagate through the remaining chambers 422B-F and out of the outlet 416.

Figure 5:
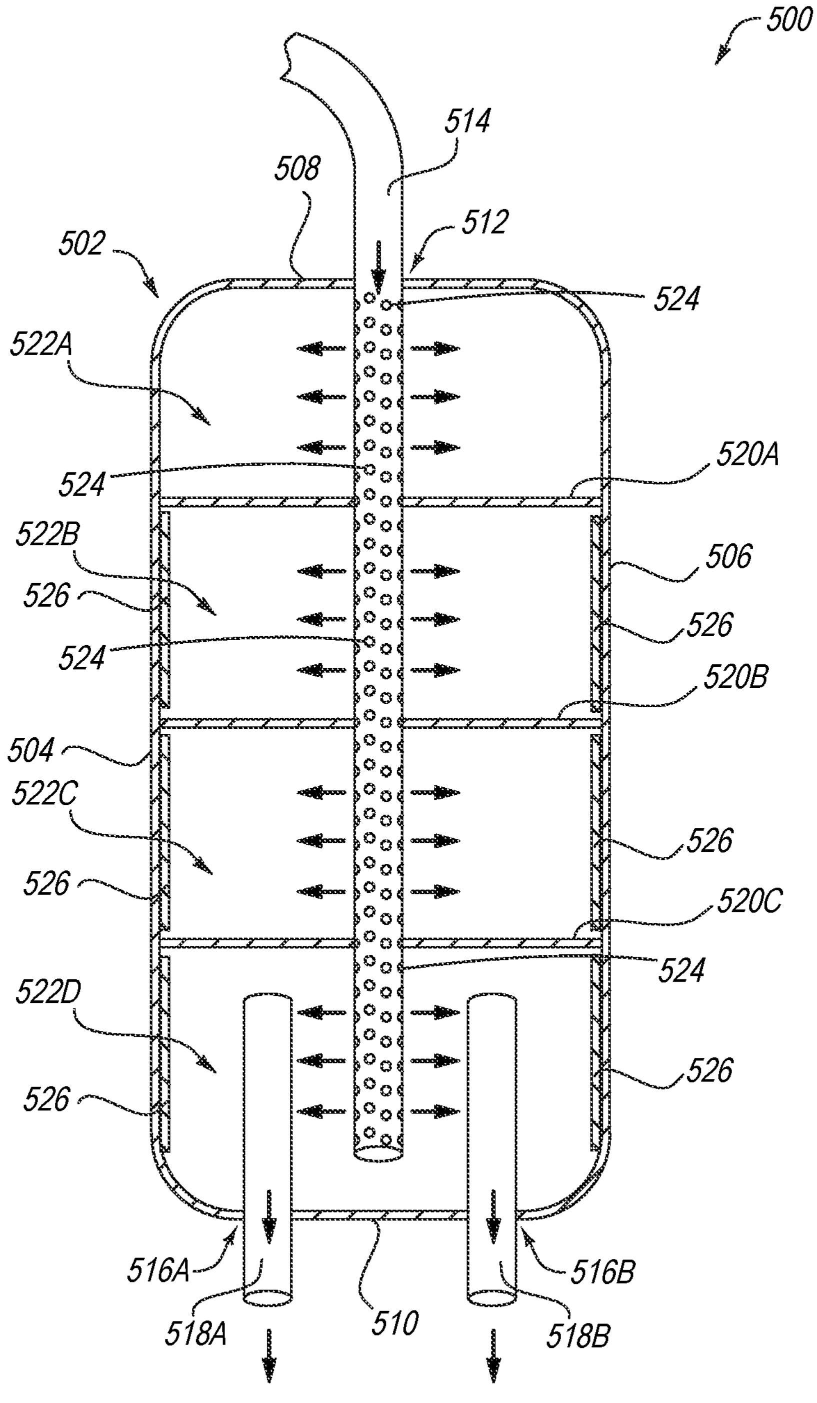
FIG. 5 is a schematic cross-section view of an acoustic silencer for a urine suction device, according to another embodiment.

FIG. 5 shows a schematic cross-section view of an acoustic silencer 500 for a urine suction device, according to another example embodiment. The acoustic silencer 500 may be used in any of the urine suction devices disclosed herein and, except as otherwise disclosed herein, may be the same as any of the silencers disclosed herein. The acoustic silencer 500 includes an enclosure 502 having a three-dimensional shape, such as, a cube, a cylinder, a cone, a sphere, an ellipsoid, another three-dimensional geometric shape, or a combination thereof. The enclosure 502 can be substantially similar to and can include some or all of the features of the enclosure 402. For example, the enclosure 502 can include a first sidewall 504, a second sidewall 506, a third sidewall 508, and a fourth sidewall 510. The third sidewall 508 can include an inlet 512 placing the acoustic silencer 500 in fluid communication with a conduit 514 (e.g., conduit 328). The fourth sidewall 510 can include one or more outlets 516A, 516B placing the acoustic silencer 500 in fluid communication with an external environment (e.g., an internal volume of the housing 308, an environment external to the housing 308, etc.). Acoustic waves within the acoustic silencer 500 can propagate or travel along a non-linear airflow path, as illustrated as directional arrows throughout the acoustic silencer 500, that extends between the inlet 512 and the one or more outlets 516 of the acoustic silencer 500. The outlet 516 can include conduits 518A, 518B that release any residual acoustic waves from the acoustic silencer 500.

In some embodiments, the acoustic silencer 500 can include one or more dividers 520A-C which separate an internal cavity of the enclosure 502 into chambers 522A-D. Each of the one or more chambers 522A-E can function as an echo chamber wherein the acoustic waves reverberate and destructively interfere to reduce or diminish the amplitude of the acoustic waves. The conduit 514 can extend into the enclosure 502 and be in fluid communication with the chambers 522A-D. For example, as shown in FIG. 5, the conduit 514 can extend through each of the dividers 520A-C and include perforations or through-holes 524 that enable one or more acoustic waves to propagate between the conduit 514 and each of the chambers 522A-D. While perforation or through-holes 524 are illustrated in FIG. 5, the conduit 514 can alternatively, or additionally, include one or more slots or any other opening having a different geometry than illustrated that places the conduit 514 in fluid communication with one or more of the chambers 522A-D.

The acoustic silencer 500 can include a material 526 disposed within the enclosure 502, for example, the material 526 can be positioned adjacent at least one of the first, second, third, or fourth sidewalls 504, 506, 508, 510. The material 526 can dampen or attenuate at least a portion of the one or more acoustic waves that propagate within the enclosure 502. In some embodiments, the material 526 can include at least one of a foam (e.g., open-cell foam), a spun-fiber (e.g., mineral wool), or a polyester. The material 526 can be adhered, fastened, molded, or otherwise affixed to any surface within the enclosure 502, such as, the first, second, third, or fourth sidewalls 504, 506, 508, 510, the conduit 514, the one or more dividers 520A-C, the one or more outlets 516A, 516B, or a combination thereof.

In some embodiments, the non-linear airflow path can be a singular path along which acoustic waves are directed to travel within the acoustic silencer 500. For example, the acoustic waves can enter the acoustic silencer through a single inlet (e.g., inlet 512) and exit the acoustic silencer 500 through a single outlet (e.g., one of outlets 516A, 516B). However, in some examples, the acoustic waves can enter through more than one inlet and exit through one or more outlets. Additionally, or alternatively, components and/or structures disposed within the acoustic silencer 500 can define a plurality of non-linear airflow paths within the acoustic silencer 500. In other words, while the non-linear airflow path is described as a singular path in some embodiments, the non-linear airflow path can include multiple paths that diverge and/or intersect.

Figure 6:
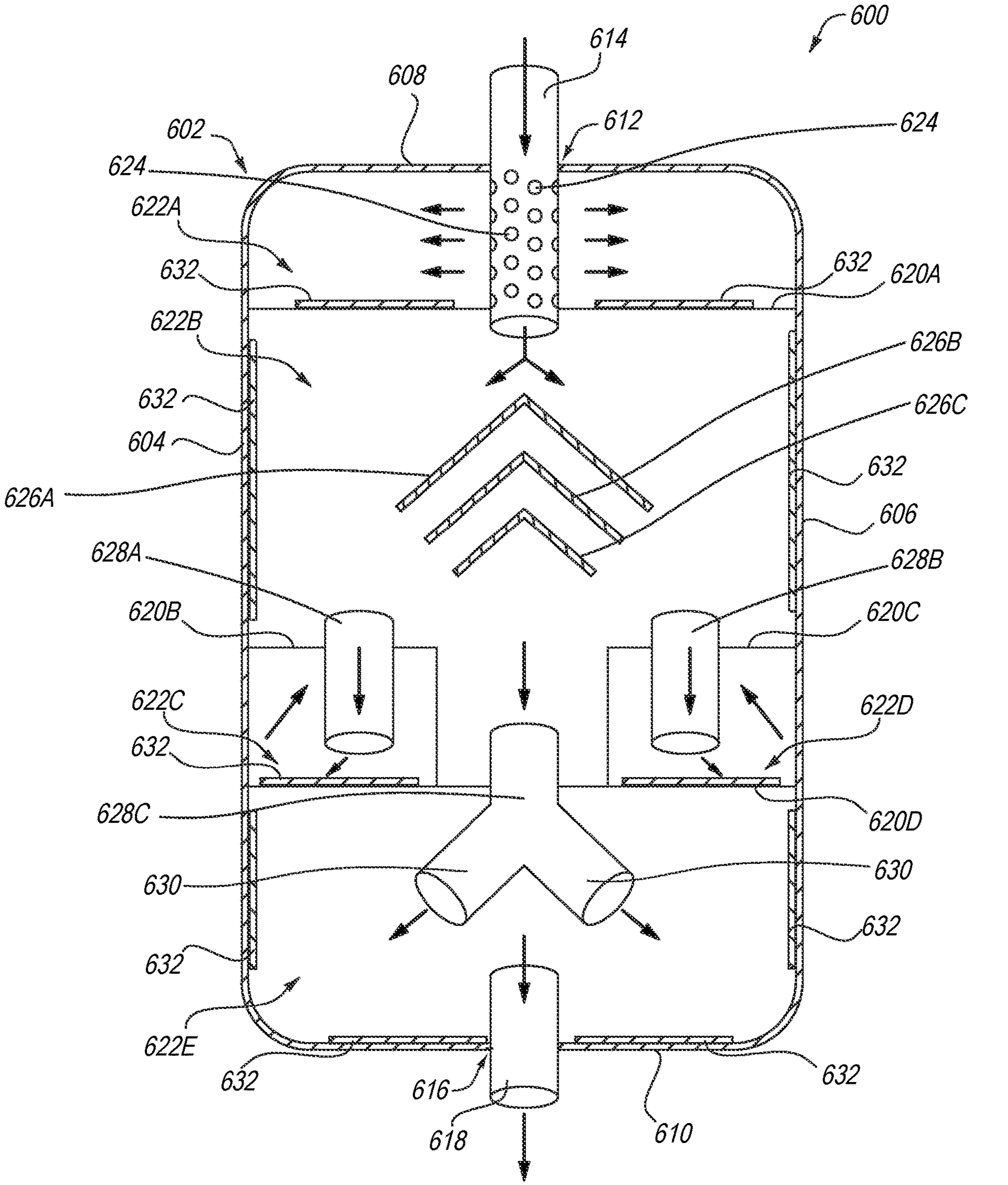
FIG. 6 is a schematic cross-section view of an acoustic silencer for a urine suction device, according to another embodiment.

FIG. 6 shows a schematic cross-section view of an acoustic silencer 600 for a urine suction device, according to yet another example embodiment. The acoustic silencer 600 may be used in any of the urine suction devices disclosed herein and, except as otherwise disclosed herein, may be the same as any of the silencers disclosed herein. The acoustic silencer 600 includes an enclosure 602 having a three-dimensional shape, such as, a cube, a cylinder, a cone, a sphere, an ellipsoid, another three-dimensional geometric shape, or a combination thereof. The enclosure 602 can be substantially similar to and can include some or all of the features of the enclosures 402, 502. For example, the enclosure 602 can include a first sidewall 604, a second sidewall 606, a third sidewall 608, and a fourth sidewall 610. The third sidewall 608 can include an inlet 612 placing the acoustic silencer 600 in fluid communication with a conduit 614 (e.g., conduit 328). The fourth sidewall 610 can include an outlet 616 and a conduit 618 placing the acoustic silencer 600 in fluid communication with an external environment (e.g., an internal volume of the housing 308, an environment external to the housing 308, etc.). Acoustic waves within the acoustic silencer 600 can propagate or travel along a non-linear airflow path that extends between the conduit 614 and the conduit 618 of the acoustic silencer 600.

In some embodiments, the acoustic silencer 600 can include one or more dividers 620A-D which separate an internal cavity of the enclosure 602 into chambers 622A-E. Each of the one or more chambers 622A-E can function as an echo chamber wherein the acoustic waves reverberate and destructively interfere to reduce or diminish the amplitude of the acoustic waves. The conduit 614 can extend into the enclosure 602 and can be directly or indirectly in fluid communication with the chambers 622A-E. For example, as shown in FIG. 6, the conduit 614 can extend through the dividers 620A and include perforations or through-holes 624 that enable one or more acoustic waves to propagate between the conduit 614 and each of the chambers 622A, 622B. While perforation or through-holes 624 are illustrated in FIG. 6, the conduit 614 can alternatively, or additionally, include one or more slots or any other opening that places the conduit 614 in fluid communication with one or more of the chambers 622A-E.

The acoustic silencer 600 can include one or more components or structures within the enclosure 602 that can direct or redirect propagation of the acoustic waves, for example, the acoustic silencer 600 can include one or more baffles 626A-C. The baffles 626A-C can be substantially similar to and can include some or all of the features of the baffles 426A-E. For example, each of the baffles 626A-C can include planar surfaces, curved surfaces, angled surfaces, perforated surfaces, slotted surfaces, or combinations thereof. Each of the baffles 626A-C can be stacked or positioned adjacent one another such that acoustics waves repeatedly reflected between surfaces of the baffles 626A-C.

In some embodiments, the acoustic silencer 600 can include one or more internal conduits 628A, 628B that direct acoustic waves into the partially enclosed portions of the enclosure 602. For example, the internal conduit 628A can direct one or more acoustic waves into the chamber 622C. The one or more acoustic waves can reflect and destructively interfere with one another while within the chamber 622C and while entering/exiting the chamber 622C through the internal conduit 628A. The internal conduit 628B can direct one or more acoustic waves into the chamber 622D. The one or more acoustic waves can reflect and destructively interfere with one another while within the chamber 622D and while entering/exiting the chamber 622D through the internal conduit 628B. In some embodiments, one or both of the internal conduits 628A, 628B can include perforation or through-holes along at least a partial length of the internal conduits 628A, 628B.

In embodiments, the acoustic silencer 600 can include an internal conduit 628C that forms multiple paths for the one or more acoustic waves to propagate. For example, the internal conduit 628C can include multiple passages 630 that direct the one or more acoustic waves to propagate to either side of the outlet 616 such that the acoustic waves are forced to propagate within the chamber 622E before exiting the enclosure 602 through the outlet 616.

The acoustic silencer 600 can include a material 632 disposed within the enclosure 602, for example, the material 632 can be positioned adjacent at least one of the first, second, third, or fourth sidewalls 604, 606, 608, 610. The material 632 can dampen or attenuate at least a portion of the one or more acoustic waves that propagate within the enclosure 602. In some embodiments, the material 632 can include at least one of a foam (e.g., open-cell foam), a spun-fiber (e.g., mineral wool), or a polyester. The material 632 can be adhered, fastened, molded, or otherwise affixed to any surface within the enclosure 602, such as, the first, second, third, or fourth sidewalls 604, 606, 608, 610, the conduit 614, the one or more dividers 620A-D, the one or more internal conduits 628A, 628B, 628C, the outlet 616, or a combination thereof.

In some embodiments, the non-linear airflow path can be a singular path along which acoustic waves are directed to travel within the acoustic silencer 600. For example, the acoustic waves can enter the acoustic silencer through a single inlet (e.g., inlet 612) and exit the acoustic silencer 600 through a single outlet (e.g., outlet 616). However, in some examples, the acoustic waves can enter through more than one inlet and exit through one or more outlets. Additionally, or alternatively, components and/or structures disposed within the acoustic silencer 600 can define a plurality of non-linear airflow paths within the acoustic silencer 600. In other words, while the non-linear airflow path is described as a singular path in some embodiments, the non-linear airflow path can include multiple paths that diverge and/or intersect.

FIGS. 4-6 illustrate example embodiments of acoustic silencers having one or more structures, components, and/or features. While various embodiments of the acoustic silencers have been described above, it should be understood that they have been presented by way of example only, and not limitation. Various changes in form and detail may be made. For example, although various embodiments have been described as having particular features and/or combinations of components, other embodiments are possible having any combination or sub-combination of any features and/or components from any of the embodiments described herein. In addition, the specific configurations of the various components can also be varied. For example, the size and specific shape of the various components can be different than the embodiments shown, while still providing the functions as described herein.

Figure 7:
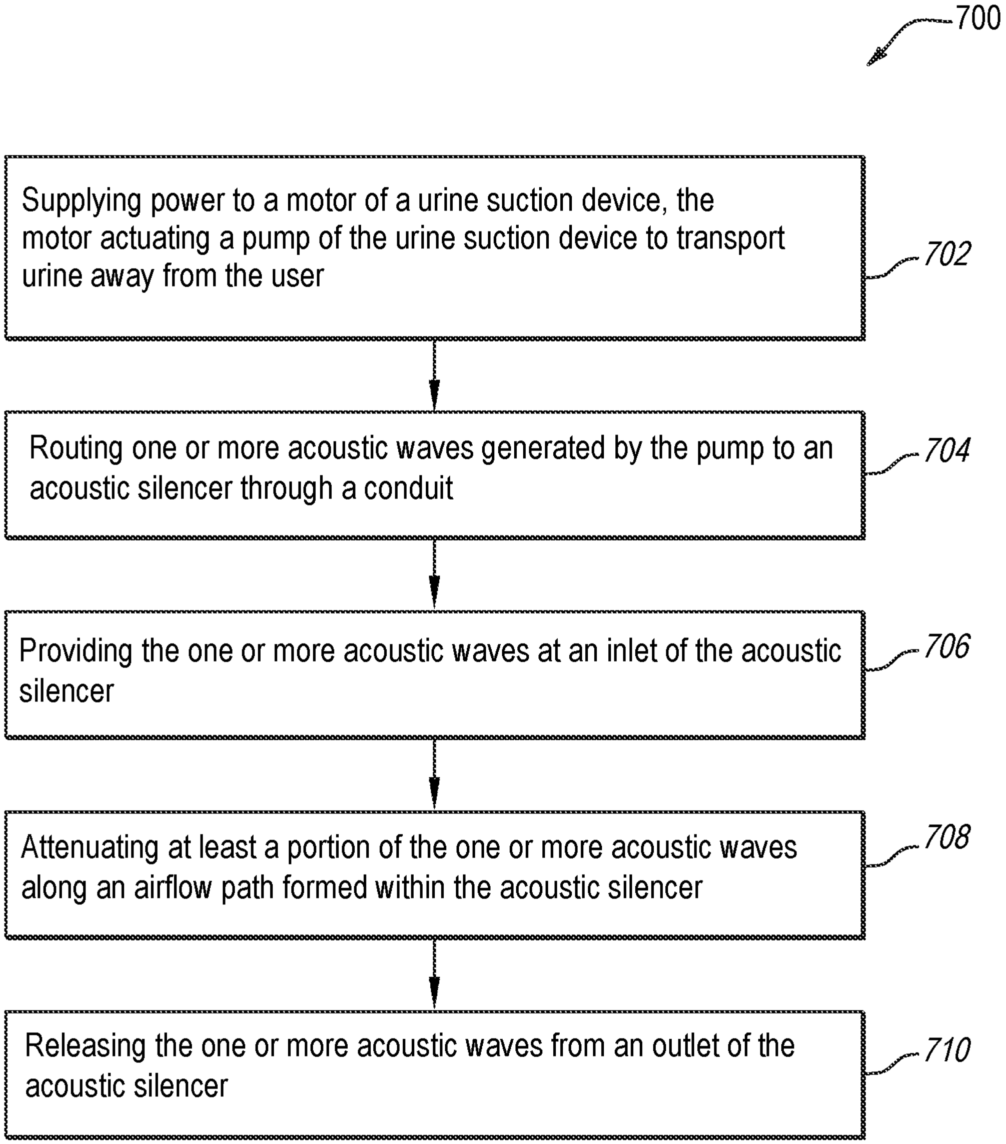
FIG. 7 is an example flow diagram of a method for reducing noise pollution of a urine suction device.

FIG. 7 illustrates an example method 700 for reducing noise pollution of a urine suction device. The suction device can be substantially similar to, and can include some or all of the features and/or components of the suction devices described herein, such as suction devices 100, 200, 300. For example, the suction device can include a motor, a pump, one or more speakers, a controller, a power supply, one or more sensors, and/or any other component of the other suction devices disclosed herein. The acoustic silencer can be substantially similar to, and can include some or all of the features and/or components of the acoustic silencers described herein, such as acoustic silencers 400, 500, 600. For example, the acoustic silencer can include one or more inlets, one or more outlets, one or more conduits, one or more baffles, one or more dividers, one or more chambers, a material that dampens acoustic waves, or a combination thereof.

The method 700 includes the act 702 of supplying power (e.g., electrical power, pneumatic power, etc.) to a motor of a urine suction device, the motor actuating a pump of the urine suction device to transport urine away from the user. The method 700 includes the act 704 of routing one or more acoustic waves generated by the pump to an acoustic silencer through a conduit. The method 700 includes the act 706 of providing the one or more acoustic waves at an inlet of the acoustic silencer. The method 700 can include the act 708 of attenuating at least a portion of the one or more acoustic waves along an airflow path formed within the acoustic silencer. The method 700 can include the act 710 of releasing the one or more acoustic waves from an outlet of the acoustic silencer.

Accordingly, the method 700 can be utilized to attenuate or reduce noise generated by operation of the motor and/or pump within the suction device. The method 700 can include more acts than the acts 702-710.

The method 700 includes the act 702 of supplying power to a motor of a urine suction device, the motor actuating a pump of the urine suction device to transport urine away from the user. In some embodiments, the power can be supplied directly to the motor as electrical power from a power supply. Alternatively, or additionally, the electrical power can be supplied to the motor through a controller coupled to the power supply. In some embodiments, the motor can be driven by air, such as, compressed air supplied to the motor. The motor can be substantially similar to, and can include some or all of the features and/or components of the motors described herein, such as motor 110, 310. For example, the motor can operate on alternating current (AC) or direct current (DC) and can be a brushless motor or a brushed motor. Additionally, or alternatively, the motor can be DC series motor, a DC shunt motor, a stepper motor, a linear motor, a servo motor, a combination thereof, or any other motor capable of the functionality described herein. Similarly, the pump can be substantially similar to, and can include some or all of the features and/or components of the pumps described herein, such as pumps 112, 312. For example, the pump can be a rotary lobe or gear pump, a diaphragm pump, a piston, a screw pump, a combination thereof, or any other pump capable of the functionality described herein.

The method 700 includes the act 704 of routing one or more acoustic waves generated by the pump to an acoustic silencer through a conduit. The method 700 includes the act 706 of providing the one or more acoustic waves at an inlet of the acoustic silencer. In embodiments, the conduit can extend from the pump and through the inlet of the acoustic silencer. The inlet can form a projection which is received within or surrounds a portion of the conduit to place the conduit in fluid communication with the acoustic silencer. The inlet can be any structure or element enabling fluid communication between the acoustic silencer and the conduit.

The method 700 can include the act 708 of attenuating at least a portion of the one or more acoustic waves along an airflow path formed within the acoustic silencer. In some embodiments, the acoustic silencer can include an enclosure and one or more components which attenuate at least a portion of acoustic waves that propagate into the enclosure. For example, the acoustic silencer can include noise dampening materials, such as, foam, mineral wool, polyester, and/or any other material known to dampen or attenuate acoustic waves. Additionally, or alternatively, the acoustic silencer can include one or more components which attenuate acoustic waves within the enclosure by redirecting the acoustic waves to generate destructive interference. In other words, one or more components or structures within the acoustic silencer can direct the acoustic waves along the airflow path which attenuates the acoustic waves as they propagate within the acoustic silencer. For example, the acoustic silencer can include multiple internal chambers, one or more conduits, one or more baffles, internal walls, plates, a combination thereof, or any other element capable of directing acoustic waves along the airflow path.

In some embodiments, the method 700 can include the act 710 of releasing the one or more acoustic waves from an outlet of the acoustic silencer. The outlet can place the acoustic silencer in fluid communication with an external environment (e.g., an internal volume of the housing 308, an environment external to the housing 308, etc.). For example, the outlet can release any residual acoustic waves from the acoustic silencer. The outlet 416 can be any structure or element enabling fluid communication between the acoustic silencer and an environment external to the acoustic silencer.

While various embodiments of the urine suction systems and devices have been described above, it should be understood that they have been presented by way of example only, and not limitation. Those of ordinary skill in the art having the benefit of this disclosure would recognize that the ordering of certain steps may be modified and such modifications are in accordance with the variations of the invention. Additionally, certain of the steps may be performed concurrently in a parallel method when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. In addition, the specific configurations of the various components can also be varied. For example, the size and specific shape of the various components can be different than the embodiments shown, while still providing the functions as described herein.

The invention claimed is:

1. A urine suction device, comprising:

a housing defining an interior volume, the housing defining a recess configured to receive a container, the housing not configured to cover a top of the container, the recess distinct and at least partially spaced from the interior volume;

a motor disposed in the interior volume;

a pump disposed in the interior volume, the pump configured to be driven by the motor, the pump being configured to extract urine from a urine collection device;

one or more conduits disposed in the interior volume, the one or more conduits coupled to the pump and configured to exhaust a fluid from the pump; and an acoustic silencer disposed in the interior volume, the acoustic silencer in fluid communication with the one or more conduits and the pump, the acoustic silencer defining a non-linear airflow path between an inlet and an outlet of the acoustic silencer, the acoustic silencer including:

an enclosure defining the inlet and the outlet, the one or more conduits extending through the inlet;

one or more dividers separating the enclosure into two or more chambers, the one or more dividers defining at least one aperture providing fluid communication between the two or more chambers; and at least one branched internal conduit distinct and separate from the one or more conduits, the at least one branched internal conduit in fluid communication with a plurality of the two or more chambers of the enclosure, the at least one branched internal conduit is branched downstream of an inlet of the at least one branched internal conduit to form multiple paths through the at least one branched internal conduit; and wherein the one or more conduits include s a portion extending through the inlet, into the enclosure, and into a plurality of the two or more chambers, the portion of the one or more conduits defines one or more perforations in a side wall thereof, the one or more perforations in fluid communication with the plurality of the two or more chambers.

2. The urine suction device of claim 1, wherein the one or more conduits includes a first conduit and the acoustic silencer further includes:

a second conduit in fluid communication with the two or more chambers.

3. The urine suction device of claim 1, wherein the acoustic silencer further includes one or more baffles disposed in one or more of the two or more chambers, the baffles spaced from the one or more conduits and defining a gap between the one or more baffles and the enclosure.

4. The urine suction device of claim 3, wherein the at least one baffle at least partially extends from a first sidewall of the enclosure to a second sidewall of the enclosure.

5. The urine suction device of claim 1, wherein the acoustic silencer includes a material configured to dampen acoustic waves disposed within the enclosure.

6. The urine suction device of claim 5, wherein the material is at least one of a polymer, a ceramic, or a metal.

7. The urine suction device of claim 1, wherein the acoustic silencer includes:

at least one internal conduit distinct from the one or more conduits and the at least one branched internal conduit, the at least one internal conduit in fluid communication with a plurality of the two or more chambers of the enclosure.

8. The urine suction device of claim 1, wherein the pump includes diaphragm that generates one or more acoustic waves while the pump is being driven by the motor.

9. The urine suction device of claim 1, wherein acoustic waves propagating along the airflow path are reduced by 10 dB.

10. The urine suction device of claim 1, wherein the acoustic silencer at least partially attenuates acoustic frequencies of 20 Hz to 4 kHz.

11. The urine suction device of claim 1, wherein the acoustic silencer includes a set of baffles at least partially directing the flow of acoustic waves along the non-linear airflow path.

12. The urine suction device of claim 1, wherein a majority of each of the two or more chambers is open space.

13. The urine suction device of claim 1, wherein the one or more dividers include a plurality of dividers, and the aperture of one of the plurality of dividers is closer to a side wall of the enclosure than the aperture of another one of the plurality of dividers, wherein the side wall does not define at least one inlet and at least one outlet of the enclosure.

14. The urine suction device of claim 13, wherein each of the plurality of dividers extend from one side wall of the enclosure to an opposing side wall of the enclosure.

15. The urine suction device of claim 1, wherein the one or more dividers defining at least one of the two or more chambers defines a single aperture, and wherein the at least one of the two or more chambers is only in fluid communication with the inlet, the outlet, and a remainder of the two or more chambers via the single aperture.

16. The urine suction device of claim 1, wherein the one or more conduits extend into each of the two or more chambers, the portion of the one or more conduits defines a plurality of perforations in a side wall thereof, at least one of the plurality of perforations in fluid communication with each of the two or more chambers.

17. The urine suction device of claim 1, wherein the one or more perforations include a plurality of perforations, the plurality of perforations present along substantially all of a length of the portion of the one or more conduits.

18. A system for transporting urine away from a user, the system comprising:

a urine collection device;

a container; and a urine suction device coupled to the urine collection device and configured to draw urine from the urine collection device into the container, the urine suction device comprising:

a housing defining an interior volume, the housing defining a recess configured to receive the container, the housing not configured to cover a top of the container, the recess distinct and at least partially spaced from the interior volume;

a motor disposed in the interior volume;

a pump disposed in the interior volume, the pump configured to be driven by the motor, the pump being configured to extract urine from the urine collection device;

one or more conduits disposed in the interior volume, the one or more conduits coupled to the pump and configured to exhaust a fluid from the pump; and an acoustic silencer disposed in the interior volume, the acoustic silencer in fluid communication with the one or more conduits and pump, the acoustic silencer defining a non-linear airflow path between an inlet and an outlet of the acoustic silencer, the acoustic silencer including:

an enclosure defining the inlet and the outlet, the one or more conduits extending through the inlet;

one or more dividers separating the enclosure into two or more chambers, the one or more dividers defining at least one aperture providing fluid communication between the two or more chambers; and at least one branched internal conduit distinct and separate from the one or more conduits, the at least one branched internal conduit in fluid communication with a plurality of the two or more chambers of the enclosure, the at least one branched internal conduit is branched downstream of an inlet of the at least one branched internal conduit to form multiple paths through the at least one branched internal conduit; and wherein the one or more conduits includes a portion extending through the inlet, into the enclosure, and into a plurality of the two or more chambers, the portion of the one or more conduits defines one or more perforations in a side wall thereof, the one or more perforations in fluid communication with the plurality of the two or more chambers.

19. The system of claim 18, wherein the recess retains a base portion the container.

20. The system of claim 18, wherein the acoustic silencer includes a material disposed within the enclosure and configured to dampen acoustic waves, the material being at least one of a foam, mineral wool, or polyester.

21. The system of claim 18, wherein:

the pump generates acoustic waves that travel through the one or more conduits into the acoustic silencer;

the acoustic waves have a first amplitude when entering the inlet of the acoustic silencer and a second amplitude when exiting the acoustic silencer through the outlet; and the second amplitude is less than the first amplitude.

22. The system of claim 21, wherein the second amplitude is at least 25% less than the first amplitude.

23. The system of claim 18, wherein the urine suction device includes an inlet configured to couple to the urine collection device to enable extraction of urine from the urine collection device, the inlet being in fluid communication with the pump.

24. The system of claim 18, wherein the one or more conduits includes a first conduit and the acoustic silencer further includes:

a second conduit in fluid communication with the two or more chambers.

25. A method for reducing noise pollution of a urine suction device with an acoustic silencer, the method comprising:

supplying power to a motor of the urine suction device, the motor actuating a pump of the urine suction device to transport urine away from a user;

routing one or more acoustic waves generated by the pump to the acoustic silencer through one or more conduits, the acoustic silencer including:

an enclosure defining the inlet and the outlet, the one or more conduits extending through the inlet;

one or more dividers separating the enclosure into two or more chambers, the one or more dividers defining at least one aperture providing fluid communication between the two or more chambers; and at least one branched internal conduit distinct and separate from the one or more conduits, the at least one branched internal conduit in fluid communication with a plurality of the two or more chambers of the enclosure, the at least one branched internal conduit is branched downstream of an inlet of the at least one branched internal conduit to form multiple paths through the at least one branched internal conduit;

wherein the one or more conduits includes a portion extending through the inlet, into the enclosure, and into a plurality of the two or more chambers, the portion of the one or more conduits defines one or more perforations in a side wall thereof, the one or more perforations in fluid communication with the plurality of the two or more chambers; and providing the one or more acoustic waves at an inlet of the acoustic silencer;

attenuating at least a portion of the one or more acoustic waves along an airflow path formed within the acoustic silencer; and releasing the one or more acoustic waves from an outlet of the acoustic silencer; and wherein the urine suction device includes a housing defining an interior volume, the motor, the pump, and one or more conduits, and the acoustic silencer disposed in the interior volume, the housing further defines a recess configured to receive a container, the housing not configured to cover a top of the container, the recess distinct and at least partially separate from the interior volume.

* * * * *